(12) United States Patent
Cheung et al.

(10) Patent No.: US 8,648,225 B2
(45) Date of Patent: Feb. 11, 2014

(54) PROCESS FOR HYDROGENATING HIGHLY UNSATURATED HYDROCARBONS AND CATALYST THEREFOR

(75) Inventors: Tin-Tack Peter Cheung, Kingwood, TX (US); Marvin M Johnson, Bartlesville, OK (US); Darin B. Tiedtke, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 756 days.

(21) Appl. No.: 12/758,534

(22) Filed: Apr. 12, 2010

(65) Prior Publication Data

US 2011/0251447 A1    Oct. 13, 2011

(51) Int. Cl.
| | |
|---|---|
| *C07C 5/03* | (2006.01) |
| *C07C 5/08* | (2006.01) |
| *C07C 5/10* | (2006.01) |
| *C07C 7/167* | (2006.01) |
| *B01J 23/00* | (2006.01) |
| *B01J 21/00* | (2006.01) |

(52) U.S. Cl.
USPC ........... 585/262; 585/259; 502/304; 502/326; 502/327; 502/330; 502/332; 502/333; 502/339; 502/344; 502/347; 502/348; 502/355; 502/415; 502/439

(58) Field of Classification Search
USPC ......... 502/304, 326, 327, 330, 332, 333, 339, 502/344, 347, 348, 355, 415, 439; 585/259, 585/262
See application file for complete search history.

(56) References Cited

U.S. PATENT DOCUMENTS

| | | | | |
|---|---|---|---|---|
| 3,901,947 A | * | 8/1975 | Enomoto et al. | 568/804 |
| 3,998,722 A | * | 12/1976 | Mayer et al. | 208/112 |
| 4,126,645 A | | 11/1978 | Collins | |
| 4,404,124 A | | 9/1983 | Johnson et al. | |
| 4,484,015 A | | 11/1984 | Johnson et al. | |
| 4,547,600 A | | 10/1985 | Cosyns et al. | |
| 4,547,611 A | * | 10/1985 | Jones et al. | 585/500 |
| 4,571,442 A | | 2/1986 | Cosyns et al. | |
| 4,613,714 A | | 9/1986 | Stadler et al. | |
| 4,762,956 A | | 8/1988 | Liu et al. | |
| 4,802,974 A | | 2/1989 | Kukes et al. | |
| 4,870,044 A | | 9/1989 | Kukes et al. | |
| 4,906,602 A | | 3/1990 | Schneider et al. | |
| 5,356,851 A | | 10/1994 | Sarrazin et al. | |
| 5,364,998 A | | 11/1994 | Sarrazin et al. | |
| 5,488,024 A | | 1/1996 | Cheung et al. | |
| 5,510,550 A | | 4/1996 | Cheung et al. | |
| 5,583,274 A | | 12/1996 | Cheung et al. | |
| 5,585,318 A | | 12/1996 | Johnson et al. | |
| 5,587,348 A | | 12/1996 | Brown et al. | |
| 5,698,752 A | | 12/1997 | Brown et al. | |
| 5,739,075 A | * | 4/1998 | Matusz | 502/302 |
| 5,753,583 A | | 5/1998 | Heineke et al. | |

(Continued)

OTHER PUBLICATIONS

Sato, Satoshi, Ortho-Selective Methylation of Phenol Catalyzed by Ce02-MgO Prepared by Citrate Process, Journal of Catalysis, 178 (1998), p. 264-274.

*Primary Examiner* — Cam N. Nguyen
(74) *Attorney, Agent, or Firm* — Conley Rose, P.C.; Rodney B. Carroll; Lynda S. Jolly

(57) ABSTRACT

A process for hydrogenating highly unsaturated hydrocarbons to less unsaturated hydrocarbons wherein production of saturated hydrocarbons is minimized. The process utilizes catalyst including $Ce_2O_3$, MgO, and an inorganic support, and optionally palladium, optionally silver, and/or an optional alkali metal.

38 Claims, 1 Drawing Sheet

(56) References Cited

U.S. PATENT DOCUMENTS

| | | |
|---|---|---|
| 5,866,735 A | 2/1999 | Cheung et al. |
| 5,889,187 A | 3/1999 | Than et al. |
| 5,955,397 A | 9/1999 | Didillon et al. |
| 6,790,552 B2 | 9/2004 | Kobayashi et al. |
| 7,301,062 B2 * | 11/2007 | Gartside et al. ............... 585/260 |
| 7,521,393 B2 * | 4/2009 | Blankenship et al. ......... 502/330 |
| 7,566,388 B2 * | 7/2009 | Sasaki et al. ................... 204/283 |
| 7,745,370 B2 * | 6/2010 | Blankenship et al. ......... 502/262 |
| 2006/0223698 A1 * | 10/2006 | Kawabata et al. ............. 502/304 |
| 2007/0167323 A1 * | 7/2007 | Kobayashi ..................... 502/341 |
| 2009/0288401 A1 * | 11/2009 | Kaneshiro et al. ............... 60/299 |

* cited by examiner

PROCESS FOR HYDROGENATING HIGHLY UNSATURATED HYDROCARBONS AND CATALYST THEREFOR

CROSS REFERENCE TO RELATED APPLICATIONS

Not applicable.

FEDERALLY SPONSORED RESEARCH

Not applicable.

PARTIES TO A JOINT RESEARCH AGREEMENT

Not applicable.

FIELD OF THE INVENTION

This invention relates to a catalyst composition, to a process of using such catalyst composition for hydrogenating highly unsaturated hydrocarbons to less unsaturated hydrocarbons, for isomerizing highly unsaturated hydrocarbons to other highly unsaturated hydrocarbons, and to a process of making the catalyst composition.

BACKGROUND OF THE INVENTION

It is known to one skilled in the art that a less unsaturated hydrocarbon compound can be produced by a thermal cracking process. For example, a fluid stream containing a saturated hydrocarbon such as, for example, ethane, propane, butane, pentane, naphtha, and the like and combinations thereof can be fed into a thermal (or pyrolytic) cracking furnace. Within the furnace, the saturated hydrocarbon is converted to a less unsaturated hydrocarbon compound such as, for example, ethylene or propylene. Such less unsaturated hydrocarbons are an important class of chemicals that find a variety of industrial uses. For example, ethylene can be used as a monomer or comonomer for producing a polyolefin. Other uses of unsaturated hydrocarbons are well known to one skilled in the art.

However, such less unsaturated hydrocarbon produced by a thermal cracking process generally contains an appreciable amount of less desirable highly unsaturated hydrocarbon(s) such as alkyne(s) or diolefin(s). For example, propylene produced by thermal cracking propane, natural gas liquids or other saturated hydrocarbons are generally contaminated with a highly unsaturated hydrocarbon, such as methyl acetylene. For commercial purposes, it is desirable to selectively hydrogenate the highly unsaturated hydrocarbons to a less unsaturated hydrocarbon, such as propylene, but not to a saturated hydrocarbon such as propane, in a hydrogenation reaction. Additionally, propylene produced by thermal cracking of propane, natural gas liquids or other saturated hydrocarbons may also be contaminated with a highly unsaturated hydrocarbon such as propadiene. Again, for commercial purposes, it is desirable to isomerize the propadiene to another highly unsaturated hydrocarbon, such as methyl acetylene, which may then be selectively hydrogenated to a less unsaturated hydrocarbon such as propylene, but not to a saturated hydrocarbon such as propane.

As an alternative example, ethylene produced by thermal cracking of ethane, natural gas liquids or other saturated hydrocarbons may be contaminated with a highly unsaturated hydrocarbon such as acetylene. For commercial purposes, it is desirable to selectively hydrogenate the highly unsaturated hydrocarbon to a less unsaturated hydrocarbon such as ethylene, but not to a saturated hydrocarbon such as ethane, in a hydrogenation reaction.

Catalysts comprising palladium and an inorganic support, such as alumina, are known catalysts for the hydrogenation of highly unsaturated hydrocarbons such as alkynes and/or diolefins. In the case of the selective hydrogenation of acetylene to ethylene, a palladium and silver catalyst supported on alumina can be employed. Such catalysts are disclosed in U.S. Pat. Nos. 4,404,124 and 4,484,015, the disclosures of which are incorporated herein by reference. The operating temperature for this hydrogenation process is selected to maximize hydrogenation of highly unsaturated hydrocarbon such as alkyne (e.g., acetylene) to its corresponding less unsaturated hydrocarbon such as alkene (e.g., ethylene) thereby removing the alkyne from the product stream while minimizing the amount of alkene which is hydrogenated to a saturated hydrocarbon such as alkane (e.g., ethane).

It is also generally known to those skilled in the art that impurities, such as carbon monoxide, and sulfur impurities, such hydrogen sulfide, carbonyl sulfide, carbon disulfide, mercaptans, thiophene, organic sulfides, organic disulfides, organic trisulfides, organic tetrasulfides and organic polysulfides, which are present in an alkyne-containing feed or product stream can poison and deactivate a palladium-containing catalyst. For example, carbon monoxide is well known to temporarily poison or inactivate such a hydrogenation catalyst. It is also generally known by those skilled in the art that a sulfur impurity such as a sulfur compound (such as $H_2S$, COS, mercaptans, thiophene, organic sulfides, organic disulfides and organic polysulfides), when present during the hydrogenation of highly unsaturated hydrocarbons such as diolefins (also referred to as alkadienes) or alkynes to less unsaturated hydrocarbons such as monoolefins (also referred to as alkenes), can poison and deactivate hydrogenation catalysts. This is especially true in a depropanizer hydrogenation process because the feed stream from the depropanizer being sent to the acetylene removal unit (also referred to as "ARU") of such depropanizer hydrogenation process typically contains low levels of a sulfur compound(s) with the possibility of transient spikes in the level of such sulfur compound(s). Thus, the development of a catalyst composition and its use in processes for the hydrogenation of highly unsaturated hydrocarbons such as diolefins or alkynes to less unsaturated hydrocarbons such as monoolefins in the presence of a sulfur impurity such as a sulfur compound would also be a significant contribution to the art and to the economy.

A palladium-containing "skin" catalyst in which palladium is distributed on the surface or "skin" of the catalyst has been developed which is known to be more selective and active than a non-skin catalyst in converting highly unsaturated hydrocarbons in an ethylene stream to less unsaturated hydrocarbons. Such a catalyst is disclosed, for example, in U.S. Pat. No. 4,484,015, the disclosure of which is incorporated herein by reference. It is known that the catalyst selectivity is determined, in part, by the skin thickness. Generally, catalyst selectivity decreases as the skin thickness increases. There is therefore an ever-increasing need to develop a catalyst having a better "skin" on the catalyst for a better selective hydrogenation of a highly unsaturated hydrocarbon, such as an alkyne, to a less unsaturated hydrocarbon, such as an alkene, without further hydrogenation to a saturated hydrocarbon, such as an alkane.

Methylacetylene and propadiene (collectively referred to as "MAPD") are impurities present in the front-end depropanizer ARU stream in ethylene plants. They are usually removed by selective hydrogenation. Otherwise, they are concentrated in the propylene/propane stream and must be removed by fractionation or in a secondary hydrogenation process. Excessive propylene loss occurs during fractionation when the MAPD level is high.

Hydrogenation of methylacetylene proceeds more readily than propadiene because, in many ways, propadiene behaves like propylene. The conversion of the propadiene can be increased if the propadiene is first isomerized to methylacetylene. In front-end depropanizer ARU service, palladium without promoters usually provides a good conversion of the propadiene because the palladium catalyzes the hydroisomerization of the propadiene to methylacetylene. However, it is well known that palladium catalysts without promoters are poor selective hydrogenation catalysts as far as in converting acetylene to ethylene. The selectivity is improved by the addition of silver to the palladium but the silver also drastically cuts the hydroisomerization activity of the palladium, thus greatly reducing the conversion of the propadiene.

There remains a need therefore, for a highly selective and active hydrogenation catalyst useful, for example, in front-end depropanizer ARU service. There further remains a need for a hydrogenation catalyst converting highly unsaturated hydrocarbons, such as methylacetylene into less unsaturated hydrocarbons, such as propylene. There still further remains a need for a catalyst for the isomerization of highly unsaturated hydrocarbons, such as propadiene, to another highly unsaturated hydrocarbon, such as methyl acetylene, such that the other highly unsaturated hydrocarbon may then be hydrogenated to a less unsaturated hydrocarbon. There still further remains a need for such a catalyst which does not cause significant production of saturated hydrocarbons, such as ethane.

SUMMARY OF THE EMBODIMENTS

Some embodiments provide a process for selective hydrogenation of highly unsaturated hydrocarbons to less unsaturated hydrocarbons including the step of contacting a hydrocarbon-containing fluid comprising one or more highly unsaturated hydrocarbons with a catalyst composition comprising cerium and magnesium with the contacting step occurring in the presence of hydrogen. In some embodiments, the catalyst composition is supported.

In some embodiments of the selective hydrogenation process, the highly unsaturated hydrocarbon is selected from the group of dienes, alkynes, and mixtures thereof.

In some embodiments of the selective hydrogenation process, the hydrocarbon-containing fluid comprises acetylene and methylacetylene.

Other embodiments provide a process for isomerization of highly unsaturated hydrocarbons to other highly unsaturated hydrocarbons including the step of contacting a hydrocarbon fluid containing one or more highly unsaturated hydrocarbons with a catalyst composition comprising cerium and magnesium. In some embodiments, the catalyst composition is supported.

In some embodiments of the isomerization process, the highly unsaturated hydrocarbon is selected from the group of dienes, alkynes, and mixtures thereof.

In some embodiments of the isomerization process, the hydrocarbon-containing fluid comprises acetylene and methylacetylene In some embodiments of the isomerization or selective hydrogenation processes, the catalyst composition further contains silver. In some embodiments of the isomerization or selective hydrogenation processes, the catalyst composition further includes an alkali metal.

Other embodiments provide a hydrogenation catalyst comprising cerium and magnesium having an Mg:Ce molar ratio of between about 0.01:1 to about 20:1. In some embodiments, the catalyst is supported.

Yet other embodiments provide an isomerization catalyst comprising cerium and magnesium having an Mg:Ce molar ratio of between about 0.01:1 to about 20:1. In some embodiments, the catalyst is supported.

In some embodiments, the isomerization catalyst further contains an inorganic support. In some embodiments, the hydrogenation catalyst further includes an inorganic support.

In some embodiments, the inorganic support comprises an alumina.

In some embodiments, the isomerization catalyst further comprises palladium. In some embodiments of the invention, the hydrogenation catalyst further comprises palladium. As noted above, any of the aforementioned and below mentioned embodiments may be supported or unsupported.

One embodiment of the invention provides a process for producing a catalyst in which a cerium-containing compound, a magnesium-containing compound, a citric acid component, and water are mixed, the mixture then subjected to melting conditions, and the molten mixture then subjected to evaporating conditions.

In yet other embodiments of the invention, a cerium-containing compound, a magnesium-containing compound, a citric acid component, and water are mixed, the mixture then subjected to melting conditions, the molten mixture contacted with an inorganic support, subjecting the inorganic support and molten mixture to drying conditions and then to calcining conditions to obtain a calcined catalyst. In some embodiments of the invention, the calcined catalyst is contacted with an aqueous palladium solution and then dried to produce a palladium containing catalyst. In some embodiments, the palladium containing catalyst is then contacted with an aqueous silver solution, then dried and then calcined.

DESCRIPTION OF EMBODIMENTS OF THE INVENTION

Figure 1:
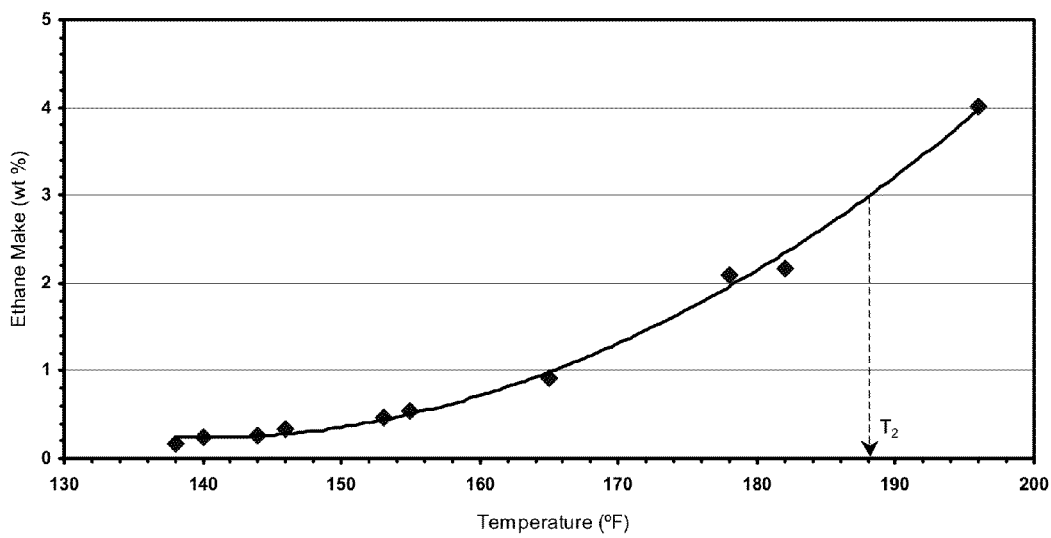
FIG. 1 is a graph of ethane production as a function of temperature for Sample M discussed in Example 11.

As used herein, the term "fluid" denotes gas, liquid, vapor, or combinations thereof. The term "cerium" refers to cerium metal and cerium oxides. The term "magnesium" refers to magnesium metal and magnesium oxides. The term "palladium" refers to palladium metal and palladium oxides. The term "silver" refers to silver metal and silver oxides.

The term "supported" refers to a catalyst composition that comprises an inorganic support. The term "unsupported" refers to a catalyst composition that does not comprise an inorganic support.

The term "substantial" or "substantially" generally means more than trivial. Unless specified to the contrary or apparent from the plain meaning of a phrase, the word "or" has the inclusive meaning.

The term "saturated hydrocarbon" refers to any hydrocarbon that does not contain any carbon-to-carbon double bonds or carbon-to-carbon triple bonds. Examples of saturated hydrocarbons include, but are not limited to, ethane, propane, butanes, pentanes, hexanes, octanes, decanes, naphtha, and the like and combinations thereof.

The term "highly unsaturated hydrocarbon" refers to a hydrocarbon having a triple bond or two or more double bonds between carbon atoms in the molecule. Examples of highly unsaturated hydrocarbons include, but are not limited to, aromatic compounds such as benzene and naphthalene; alkynes such as acetylene, methylacetylene (also referred to as propyne), and butynes; diolefins such as propadiene, butadienes, pentadienes (including isoprene), hexadienes, octadienes, and decadienes; and the like and combinations thereof.

The term "less unsaturated hydrocarbon" refers to a hydrocarbon in which the triple bond in the highly unsaturated hydrocarbon is hydrogenated to a double bond or a hydrocarbon in which the number of double bonds is one less, or at least one less, than that in the highly unsaturated hydrocarbon. Examples of less unsaturated hydrocarbons include, but are not limited to, monoolefins such as ethylene, propylene, butenes, pentenes, hexenes, octenes, decenes, and the like and combinations thereof.

The term "hydrogenation process" refers to a process, which converts a highly unsaturated hydrocarbon such as an alkyne or a diolefin to a less unsaturated hydrocarbon such as a monoolefin or a saturated hydrocarbon such as an alkane. The term "selective" refers to such hydrogenation process in which a highly unsaturated hydrocarbon such as an alkyne or a diolefin is converted to a less unsaturated hydrocarbon such as a monoolefin without further hydrogenating the less unsaturated hydrocarbon to a saturated hydrocarbon such as an alkane. Thus, for example, when a highly unsaturated hydrocarbon is converted to a less unsaturated hydrocarbon without further hydrogenating such less unsaturated hydrocarbon to a saturated hydrocarbon, the hydrogenation process is "more selective" than when such highly unsaturated hydrocarbon is hydrogenated to a less unsaturated hydrocarbon and then further hydrogenated to a saturated hydrocarbon.

The term "depropanizer" refers to a fractionation process common in ethylene units, which separates hydrocarbons with boiling points equal to or lower than 3 carbon atom hydrocarbons from hydrocarbons with higher boiling points. The feed stream from a depropanizer refers to the overhead product from the depropanizer that comprises propylene and lighter hydrocarbons. In a depropanizer hydrogenation process, the feed stream from the depropanizer being sent to the acetylene removal unit (also referred to as "ARU") of such depropanizer hydrogenation process typically contains low levels of a sulfur compound(s) with the possibility of transient spikes in the level of such sulfur compound(s).

The term "isomerization process" refers to a process, which isomerizes a highly unsaturated hydrocarbon, such as a diolefin, to another highly unsaturated hydrocarbon, such as an alkyne, which, if desired, may be selectively hydrogenated to a less unsaturated hydrocarbon such as a monoolefin. In an embodiment, the isomerization process and hydrogenation process occur in sequential reactor vessels. In another embodiment, the isomerization process and hydrogenation process occur in the same reactor vessel.

The term "skin" refers to the exterior surface of the catalyst composition, which can contain components, such as palladium, of the catalyst composition. The skin can be any thickness as long as such thickness can promote the hydrogenation and/or isomerization process(es) discussed herein. Generally, the thickness of the skin can be in the range of from about 1 micron to about 1,000 microns, preferably in the range of from about 5 microns to about 750 microns, more preferably in the range of from about 5 microns to about 500 microns, and most preferably in the range of from 10 microns to 300 microns. Preferably, the palladium is concentrated in the skin of the catalyst composition whereas the catalyst component comprising silver or an alkali metal compound, or both silver and an alkali metal compound, is distributed throughout the catalyst composition.

According to one embodiment of this invention, a catalyst composition that can be used to selectively hydrogenate a highly unsaturated hydrocarbon (such as an alkyne or a diolefin), to a less unsaturated hydrocarbon (such as an alkene or a monoolefin) is provided. The catalyst composition comprises (a) cerium, such as cerium oxide, (b) magnesium, such as magnesium oxide, and (c) an inorganic support, such as alumina.

According to another embodiment of the invention, a catalyst composition is provided which can be used to isomerize a highly unsaturated hydrocarbon (such as a diolefin) to another highly unsaturated hydrocarbon (such as an alkyne). The catalyst composition comprises (a) cerium, such as cerium oxide, (b) magnesium, such as magnesium oxide, and (c) an inorganic support, such as alumina.

According to yet another embodiment of this invention, a catalyst composition that can be used to selectively hydrogenate a highly unsaturated hydrocarbon (such as an alkyne or a diolefin) to a less unsaturated hydrocarbon (such as an alkene or a monoolefin) is provided. The catalyst composition comprises (a) palladium such as palladium metal, palladium oxide, or combinations thereof, (b) optionally, silver and/or an alkali metal compound, and (c) cerium oxide and/or magnesium oxide. In additional embodiments, the composition comprising a support such as an inorganic material (e.g., alumina).

According to yet another embodiment of this invention, a catalyst composition that can be used to isomerize a highly unsaturated hydrocarbon (such as a diolefin) to another highly unsaturated hydrocarbon (such as an alkyne) is provided. The catalyst composition comprises (a) palladium such as palladium metal, palladium oxide, or combinations thereof, (b) optionally, silver and/or an alkali metal compound, and (c) cerium oxide and/or magnesium oxide. In additional embodiments, the composition comprising a support such as an inorganic material (e.g., alumina).

In yet another embodiment of the invention, a supported catalyst composition for selective hydrogenation and/or isomerization of highly unsaturated hydrocarbons which comprises (a) palladium such as palladium metal, palladium oxide, or combinations thereof, (b) optionally, silver and/or an alkali metal compound, and (c) cerium oxide and/or magnesium oxide, wherein the palladium can be present as "skin" on or near the surface of the catalyst support composition and the silver and/or alkali metal compound, can be distributed as skin with the palladium or throughout the catalyst composition is provided.

Generally, the cerium component of the catalyst composition may be present in any weight percent (wt %) that is effective in selectively hydrogenating a highly unsaturated hydrocarbon (such as an alkyne) to a less unsaturated hydrocarbon (such as an alkene) and/or isomerizing a highly unsaturated hydrocarbon (such as a diolefin) to another highly unsaturated hydrocarbon (such as an alkyne). Generally, the catalyst composition comprises cerium in the range of from about 0.01 weight percent cerium based on the total weight of the catalyst composition to about 15 weight percent cerium, preferably in the range of from about 0.1 weight percent cerium to about 10 weight percent cerium and, most preferably, in the range of from 0.05 weight percent cerium to 5 weight percent cerium.

Examples of suitable cerium-containing compounds suitable for preparing the catalyst composition include, but are not limited to, cerium bromide, cerium chloride, cerium fluoride, cerium iodide, cerium hydroxide, cerium nitrate hexahydrate, ammonium cerium nitrate, cerium oxide, cerium perchlorate, cerium sulfate, cerium carbonate, cerium acetate hydrate, cerium acetylacetonate hydrate, cerium 2-ethylhexanoate, cerium oxalate, cerium phosphate, cerium stearate, cerium trifluoroacetylacetonate, and the like and combinations thereof. The cerium in the cerium-containing compound can have any available oxidation state. In one embodiment of the invention, a cerium-containing compound suitable for preparing the catalyst composition is cerium nitrate hexahydrate of which most, if not all, of such cerium nitrate hexahydrate is converted to cerium oxide according to a process of preparing the catalyst composition as described herein. Some of the cerium-containing compounds may be used in the form of aqueous solutions, while others may be used in the form of non-aqueous solutions wherein the solvents, include for example, alcohols, hydrocarbons, ethers, ketones and the like.

Generally, magnesium may be present in the catalyst composition in any weight percent, which is effective in selectively hydrogenating a highly unsaturated hydrocarbon (such as an alkyne) to a less unsaturated hydrocarbon (such as an alkene) and/or isomerizing a highly unsaturated hydrocarbon (such as a diolefin) to another highly unsaturated hydrocarbon (such as an alkyne). Generally, the catalyst composition comprises magnesium in the range of from about 0.01 weight percent magnesium based on the total weight of the catalyst composition to about 15 weight percent magnesium, preferably in the range of from about 0.1 weight percent magnesium to about 10 weight percent magnesium and, most preferably, in the range of from 0.5 weight percent magnesium to 5 weight percent magnesium.

Examples of suitable magnesium-containing compounds suitable for preparing the catalyst composition include, but are not limited to, magnesium bromide, magnesium chloride, magnesium fluoride, magnesium iodide, magnesium nitrate hexahydrate, magnesium hydroxide, magnesium oxide, magnesium perchlorate, magnesium sulfate, magnesium acetate, magnesium acetylacetonate, magnesium carbonate, magnesium cyclohexanebutyrate, magnesium hexafluoroacetylacetonate, magnesium hexafluorosilicate, magnesium trifluoromethanesulfonate, magnesium trifluoroacetylacetonate and the like and combinations thereof. The magnesium in the magnesium-containing compound can have any available oxidation state. In one embodiment of the invention, the magnesium-containing compound suitable for preparing the catalyst composition is magnesium nitrate hexahydrate of which most, if not all, of such magnesium nitrate hexahydrate is converted to magnesium oxide according to a process of preparing the catalyst composition as described herein. Some of the magnesium-containing compounds may be used in the form of an aqueous solution, while others may be used in the form of non-aqueous solutions wherein the solvent include, but are not limited to, alcohols, hydrocarbons, ethers, ketones and the like.

Generally, the molar ratio of magnesium to cerium (Mg:Ce molar ratio) in a catalyst composition of the invention may be in the range of from about 0.01:1 to about 20:1, preferably in the range of from about 0.01:1 to about 15:1 and, more preferably, in the range of from 0.01:1 to 10:1.

Supported Catalyst Composition:

In any of the foregoing or below hereinmentioned embodiments, the catalyst may additionally comprise an inorganic support selected from the group consisting of alumina, titania, zirconia, and the like and combinations thereof, preferably alumina. Generally, the alumina used in the catalyst composition may be any suitable alumina such as, but not limited to, alpha alumina, beta alumina, delta alumina, eta alumina, gamma alumina, and the like and combinations thereof. Preferably, such alumina is delta alumina. The alumina may also contain minor amounts of other ingredients, such as, for example, silica in a range of from about 1 weight percent silica to about 10 weight percent silica. Generally, it is desirable to have a substantially pure alumina, preferably substantially pure delta alumina, as a starting material for preparation of the catalyst composition. The alumina used as the starting material for preparation of the catalyst composition may be made by any manner or method(s) known in the art. As an example, a suitable commercially available alumina useful in preparing the catalyst composition according to the inventive process(es) described herein are delta alumina tablets or extrudate pellets or spheres, preferably delta alumina tablets, such as those manufactured by United Catalyst Inc. (UCI), Louisville, Ky.

Generally, the surface area of the support (e.g., alumina) useful in preparation of the catalyst composition is in the range of from about 3 $m^2/g$ (as measured by the Brunauer, Emmett, Teller method, i.e. BET method) to about 400 $m^2/g$, preferably in the range of from about 10 $m^2/g$ to about 300 $m^2/g$ and, most preferably, in the range of from 50 $m^2/g$ to 200 $m^2/g$. Alternatively, the surface area can be measured by mercury intrusion. One such a method is described in ASTM UOP 578-02, entitled "Automated Pore Volume and Pore Size Distribution of Porous Substances by MERCURY Porosimetry".

The pore volume of the support (e.g., alumina) useful in preparation of the catalyst composition is generally in the range of from about 0.05 mL/g to about 2 mL/g, preferably in the range of from about 0.10 mL/g to about 1.5 mL/g and, most preferably, in the range of from 0.20 mL/g to 1 mL/g.

Generally, the average pore diameter of the support (e.g., alumina useful in preparation of the catalyst composition is in the range of from about 5 angstroms to about 5,000 angstroms, preferably in the range of from about 10 angstroms to about 2,000 angstroms and, most preferably, in the range of from 25 angstroms to 1,000 angstroms.

Supports, such as aluminas, useful in preparation of the catalyst composition may have any suitable shape or form. Preferably, such supports are in the form of tablets, pellets, extrudates, spheres, and the like and combinations thereof, more preferably tablets. The support generally has a particle size in the range of from about 0.5 millimeters (mm) to about 10 mm, preferably in the range of from about 1 mm to about 8 mm and, most preferably, in the range of from 1 mm to 6 mm.

When an inorganic support is present, cerium-containing compounds and magnesium-containing compounds may be incorporated into, onto, or with the inorganic support by any suitable means or method(s) for incorporating cerium-containing compounds and magnesium-containing compounds into, onto, or with an inorganic support which results in the formation of a metal (including Mg/Ce and/or other active catalyst metals such as palladium and siver) incorporated inorganic support which can then be dried and calcined to thereby provide the catalyst composition. Examples of means or method(s) for incorporating include, but are not limited to, impregnating, soaking, spraying, and the like and combinations thereof. In one embodiment of the invention, a support is impregnated with cerium-containing compounds and magnesium-containing compounds using any standard incipient wetness impregnation technique, including but not limited to essentially completely filling the pores of the substrate material with a solution of cerium-containing compounds and magnesium-containing compounds. The cerium- and magnesium-incorporated, preferably cerium- and magnesium-impregnated support can then be subjected to drying and high temperature calcining to produce the catalyst composition.

An example impregnating solution may be formed by dissolving the cerium-containing compounds and magnesium-containing compounds preferably in the form of cerium nitrate hexahydrate and magnesium nitrate hexahydrate in water. A slightly acidic solution may be used to aid in the dissolution of the metals. For example, the support (e.g., alumina) can be impregnated with cerium-containing compounds and magnesium-containing compounds by use of a solution containing cerium nitrate hexahydrate and magnesium nitrate hexahydrate dissolved in water.

Yet another method for incorporating cerium-containing compounds and magnesium-containing compounds into, onto, or with an inorganic support is to impregnate such inorganic support with cerium-containing compounds and magnesium-containing compounds which have been melted under a melting condition as described herein. Preferably cerium containing compounds and magnesium containing compounds in the form of salts, such as, but not limited to, chlorides, nitrates, sulfates, and the like and combinations thereof are used. Preferably, such cerium-containing compounds and magnesium-containing compounds are in the form of cerium nitrate hexahydrate and magnesium nitrate hexahydrate.

Preferably, cerium-containing compounds in the form of cerium nitrate hexahydrate and magnesium-containing compounds in the form of magnesium nitrate hexahydrate are contacted with, preferably mixed with, a citric acid component to provide a mixture comprising cerium-containing compounds, magnesium-containing compounds, and a citric acid component, more preferably a mixture comprising cerium nitrate hexahydrate, magnesium hydrate hexahydrate, and a citric acid component, which can then be subjected to melting under a melting condition as described herein to provide a molten mixture.

The amount of a citric acid component, preferably citric acid monohydrate, added to the mixture comprising the cerium-containing compounds and magnesium containing compounds generally ranges from about 0.0 wt % to about 50.0 wt %, and more preferably in the range of from about 1.0 wt % to about 40.0 wt %, based upon the total weight of the solution.

Addition of small amounts of an aqueous medium such as water to the mixture of cerium-containing compounds, magnesium-containing compounds, and a citric acid component can be used to assist in the melting of such components. Generally, the amount of an aqueous medium, if present, is an amount which provides a weight ratio of cerium-containing compounds and magnesium-containing compounds to aqueous medium in the range of from about 5:1 to about 0.1:1, preferably in the range of from about 4:1 to about 0.2:1, and more preferably in the range of from 3:0 to 0.3:1.

A melting condition as referred to herein includes a temperature below the decomposition temperature of the metal such as cerium, preferably in the form of a cerium-containing compound, or magnesium, preferably in the form of a magnesium-containing compound, or combination thereof, for a time period and at a pressure that provides for a melted metal composition such as melted cerium-containing compound or magnesium-containing composition or combination thereof, preferably a pourable melted metal composition. The term "decomposition temperature" refers to the temperature at which a metal composition is no longer soluble and is no longer suitable for preparing the catalyst composition or, if an inorganic support is present, is no longer suitable for incorporating, preferably impregnating, the metal into, onto, or with inorganic support according to the inventive process(es) disclosed herein. The term "melted metal composition" refers to a metal composition or mixture of metal compounds that has been subjected to a melting condition below the decomposition temperature of the metal and has a viscosity at which the metal composition may flow.

The temperature below the decomposition temperature of a metal compound such as cerium-containing compound or magnesium-containing compound or combination thereof varies depending on the metal compound but such temperature should be such as to provide a melted metal composition. Such temperature is generally in the range of from about 25° C. to about 160° C., preferably in the range of from about 30° C. to about 150° C., more preferably in the range of from about 35° C. to about 140° C. and, most preferably, in the range of from 35° C. to 130° C.

Such melting condition also include a time period generally in the range of from about 1 minute to about 2 hours, preferably in the range of from about 5 minutes to about 1.5 hours and, most preferably, in the range of from 5 minutes to 1 hour. Such melting condition also includes a pressure generally in the range of from about atmospheric (i.e., about 14.7 pounds per square inch absolute) to about 150 pounds per square inch absolute (psia), preferably in the range of from about atmospheric to about 100 psia, most preferably about atmospheric, so long as the desired temperature can be maintained.

Unsupported Catalyst Composition:

If an inorganic support is not present, the melted cerium-containing compound, magnesium-containing compound and citric acid mixture may be subjected to evaporation using any suitable evaporator such as a rotary evaporator under an evaporating condition to provide a solidified, expanded composition comprising cerium and magnesium which can then be dried under a drying condition as disclosed herein followed by calcining under a calcining condition as disclosed herein to provide an unsupported catalyst composition.

In one embodiment of the invention, a method of preparing an unsupported catalyst composition is provided in which a molten mixture of cerium nitrate hexahydrate, magnesium nitrate hexahydrate, citric acid monohydrate, and distilled water is subjected to an evaporating condition, as disclosed herein, followed by drying the evaporated material, as disclosed herein, followed by calcining, as disclosed herein, to provide an unsupported catalyst composition.

Such evaporating condition comprises a temperature, pressure and time period effective in providing an unsupported catalyst composition. Generally, such a temperature is in the range of from about 30° C. to about 200° C., preferably in the range of from about 40° C. to about 180° C., and more preferably in the range of from 50° C. to 170° C. Generally, a time period of such evaporation condition is in the range of from about 1 minute to about 4 hours, preferably in the range of from about 5 minutes to about 3 hours, and more preferably in the range of from 5 minutes to 2 hours. Generally, a pressure of such evaporation condition is in the range of from about atmospheric (i.e., about 14.7 pounds per square inch absolute) to about 150 pounds per square inch absolute (psia), preferably about atmospheric, as long as the desired temperature can be maintained. The thus-evaporated material comprising cerium and magnesium can then be subjected to drying under a drying condition as disclosed herein followed by calcining under a calcining condition as disclosed herein to provide an unsupported catalyst composition.

Supported Catalyst Composition:

When an inorganic support is present, the melted cerium-containing compound, magnesium-containing compound, and citric acid mixture are then used to incorporate, preferably impregnate, the melted metal composition into, onto, or with an inorganic support. The melted metals comprising cerium and magnesium are incorporated, preferably impregnated, into, onto, or with the inorganic support by adding such melted metals to the inorganic support by pouring such melted metals onto the surface of the inorganic support by any manner or method(s) which results in substantially all the surface area of the inorganic support being coated with the melted metals. Preferably, such melted metals are poured over the surface of the inorganic support while the inorganic support is under constant stirring or tumbling.

It can be desirable to pre-heat the inorganic support before the melted metal composition is poured over the surface of the inorganic support. For example, in one embodiment of the invention, an support may be pre-heated to a temperature ranging from about 80° C. to about 150° C., preferably from about 85° C. to about 140° C. and, more preferably, from about 90° C. to about 130° C. The support may be pre-heated for a time period generally in the range of from about 1 minute to about 2 hours, preferably in the range of from about 5 minutes to about 1.5 hours and, most preferably, in the range of from 5 minutes to 1 hour. The support may be subjected to a pressure generally in the range of from about atmospheric (i.e., about 14.7 pounds per square inch absolute) to about 150 pounds per square inch absolute (psia), preferably in the range of from about atmospheric to about 100 psia, most preferably about atmospheric, so long as the desired temperature can be maintained. The metal-incorporated, preferably metal-impregnated, support may be further heated near the melting point of the cerium and magnesium metals for a time period in the range of from about 0.5 hour to about 15 hours, preferably in the range of from about 1 hour to about 8 hours and, most preferably, in the range of from 1 hour to 5 hours.

In a more preferred method of preparing the supported catalyst composition, a molten mixture of cerium nitrate hexahydrate, magnesium nitrate hexahydrate, citric acid monohydrate, and distilled water is used to impregnate the cerium of such melted cerium nitrate hexahydrate and magnesium of such melted magnesium hydrate into, onto, or with the support. The cerium and magnesium of such melted cerium nitrate hexahydrate and magnesium nitrate hexahydrate are impregnated into, onto, or with the support by adding such melted hydrates to the support by pouring such melted hydrates onto the surface of the support by any manner or method(s) which results in substantially all the surface area of the support being coated with the melted cerium nitrate hexahydrate and magnesium nitrate hexahydrate. Preferably, such melted hydrates are poured over the surface of the support while the alumina is under constant stirring or tumbling. The metal-incorporated support can then be subjected to drying under a drying condition as disclosed herein followed by calcining under a calcining condition as disclosed herein to provide an embodiment of the inventive catalyst composition.

Drying/Calcining Catalyst Composition:

Generally, the drying condition as referred to herein comprises a temperature in the range of from about 100° C. to about 290° C., preferably in the range of from about 110° C. to about 275° C. and, more preferably, in the range of from 120° C. to 250° C. Such drying condition also comprises a time period generally in the range of from about 0.5 hour to about 60 hours, preferably in the range of from about 1 hour to about 40 hours and, more preferably, in the range of from 1.5 hours to 20 hours. Such drying condition also comprises a pressure generally in the range of from about atmospheric (i.e., about 14.7 pounds per square inch absolute) to about 150 pounds per square inch absolute (psia), preferably in the range of from about atmospheric to about 100 psia, most preferably about atmospheric, so long as the desired temperature can be maintained. Any drying method(s) known to one skilled in the art such as, for example, air drying, heat drying, and the like and combinations thereof can be used.

Generally, the calcining condition as referred to herein comprises a temperature in the range of from about 400° C. to about 1,000° C., preferably in the range of from about 450° C. to about 800° C., and, more preferably, in the range of from 500° C. to 700° C. Such calcining condition also comprises a pressure, generally in the range of from about 7 pounds per square inch absolute (psia) to about 750 psia, preferably in the range of from about 7 psia to about 450 psia and, most preferably, in the range of from 7 psia to 150 psia, and a time period in the range of from about 1 hour to about 60 hours, preferably for a time period in the range of from about 2 hours to about 20 hours and, more preferably, for a time period in the range of from 3 hours to 15 hours.

Optional Palladium Addition:

In another embodiment of the invention, the supported or unsupported catalyst composition further includes palladium. Generally, palladium can be present in the catalyst composition in any weight percent so long as the palladium is substantially concentrated as skin on or near the surface of the catalyst composition, and that such weight percent is effective in selectively hydrogenating a highly unsaturated hydrocarbon (such as an alkyne) to a less unsaturated hydrocarbon (such as an alkene). Generally, the catalyst composition comprises palladium in the range of from about 0.0001 weight percent palladium based on the total weight of the catalyst composition to about 3 weight percent palladium, preferably in the range of from about 0.0005 weight percent palladium to about 1.5 weight percent palladium and, most preferably, in the range of from 0.001 weight percent palladium to 1.0 weight percent palladium.

Examples of suitable palladium compounds which can be used for incorporating the palladium of such palladium compounds into, onto, or with an inorganic support include, but are not limited to, palladium bromide, palladium chloride, palladium iodide, palladium nitrate, palladium nitrate hydrate, tetraamine palladium nitrate, palladium oxide, palladium oxide hydrate, palladium sulfate, palladium trifluoroacetate, tetraamminepalladium nitrate, tetraamminepalladium, potassium hexachloropalladate, potassium tetrabromopalladate, potassium tetrachloropalladate, sodium hexachloropalladate, sodium tetrachloropalladate, ammonium hexachloropalladate, ammonium tetrachloropalladate, dichlorodiammine palladium, palladium acetate, palladium acetylacetonate, and the like and combinations thereof. The palladium can have any available oxidation state. The presently preferred palladium compound is palladium chloride. Most preferably, hydrochloric acid is added to such palladium chloride ($PdCl_2$) to form a $H_2PdCl_4$ complex. When added to the support by impregnation from solution, some of the compounds can be added from aqueous solution, but others will require non-aqueous solvents such as alcohols, hydrocarbons, ethers, ketones and the like.

One can use any suitable method to determine the concentration of the palladium in the skin of the catalyst composition. Determining the concentration of the palladium in the skin of the catalyst composition also helps in determining the thickness of the skin. One technique currently favored is the electron microprobe, which is known to one skilled in the art. Another technique involves breaking open a representative sample of the catalyst composition (in catalyst particle form) and treating the catalyst particles with a dilute alcoholic solution of N,N-dimethyl-para-nitrosoaniline. The treating solution reacts with the palladium to give a red color that can be used to evaluate the distribution of the palladium. Another technique for measuring the concentration of the palladium in the skin of the catalyst composition involves breaking open a representative sample of catalyst particles followed by treatment with a reducing agent such as, for example, hydrogen, to change the color of the skin to evaluate the distribution of the palladium.

Optional Silver Addition:

The supported or unsupported catalyst composition may optionally comprise silver. Silver may be present in the catalyst composition in any weight percent as long as such weight percent is effective in selectively hydrogenating a highly unsaturated hydrocarbon (such as an alkyne) to a less unsaturated hydrocarbon (such as an alkene). Generally, the catalyst composition comprises silver in the range of from about 0.0001 weight percent silver based on the total weight of the catalyst composition to about 20 weight percent silver, preferably in the range of from about 0.003 weight percent silver to about 10 weight percent silver and, most preferably, in the range of from 0.003 weight percent silver to 5 weight percent silver. Generally, the weight ratio of silver to palladium (Ag:Pd weight ratio) in the catalyst composition can be in the range of from about 0.1:1 to about 20:1, preferably in the range of from about 1:1 to about 10:1 and, most preferably, in the range of from 3:1 to 8:1.

Suitable examples of silver compounds for use in incorporating, preferably impregnating, the silver of such silver compound(s) into, onto, or with the inorganic support include, but are not limited to, silver nitrate, silver acetate, silver cyanide and the like and combinations thereof. The presently preferred silver compound is silver nitrate.

In lieu of silver or in addition to silver, the catalyst composition can additionally comprise a catalyst component comprising an alkali metal compound. Any alkali metal-containing compound(s) can be used in the catalyst composition as long as the resulting catalyst composition is effective in selectively hydrogenating a highly unsaturated hydrocarbon (such as an alkyne) to a less unsaturated hydrocarbon (such as an alkene). Suitable examples of alkali metal compounds for use in incorporating, preferably impregnating, the alkali metal compound(s) into, onto, or with the inorganic support generally include, but are not limited to, alkali metal halides, alkali metal hydroxides, alkali metal carbonates, alkali metal bicarbonates, alkali metal nitrates, alkali metal carboxylates, and the like and combinations thereof. Preferably, the alkali metal compound is an alkali metal halide, more preferably the alkali metal compound is an alkali metal iodide or an alkali metal fluoride. Generally, the alkali metal of such alkali metal compound is selected from the group consisting of potassium, rubidium, cesium, and the like and combinations thereof. Preferably, the alkali metal of such alkali metal compound is potassium. Preferably, the alkali metal compound is potassium iodide (KI) and, more preferably, the alkali metal compound is potassium fluoride (KF).

Further examples of suitable alkali metal compounds include sodium fluoride, potassium fluoride, lithium fluoride, rubidium fluoride, cesium fluoride, sodium iodide, potassium iodide, lithium iodide, rubidium iodide, cesium iodide, sodium chloride, potassium chloride, lithium chloride, rubidium chloride, cesium chloride, sodium bromide, potassium bromide, lithium bromide, rubidium bromide, cesium bromide, sodium hydroxide, potassium hydroxide, lithium hydroxide, rubidium hydroxide, cesium hydroxide, sodium oxide, potassium oxide, lithium oxide, rubidium oxide, cesium oxide, sodium carbonate, potassium carbonate, lithium carbonate, rubidium carbonate, cesium carbonate, sodium nitrate, potassium nitrate, lithium nitrate, rubidium nitrate, cesium nitrate, and the like and combinations thereof.

Generally, the catalyst composition comprises alkali metal in the range of from about 0.001 weight percent alkali metal to about 10 weight percent alkali metal based on the total weight of the catalyst composition. Preferably, the catalyst composition comprises alkali metal in the range of from about 0.005 weight percent alkali metal to about 5 weight percent alkali metal and, most preferably, in the range of from 0.01 weight percent alkali metal to 2 weight percent alkali metal. Generally, the weight ratio of alkali metal to palladium is in the range of from about 0.05:1 to about 500:1. Preferably, the weight ratio of alkali metal to palladium is in the range of from about 0.1:1 to about 200:1 and, most preferably, in the range of from 0.2:1 to 100:1.

When the alkali metal compound is an alkali metal iodide, the catalyst composition comprises alkali metal iodide in the range of from about 0.03 weight percent iodine (chemically bound as iodide) (on a total catalyst composition weight basis) to about 10 weight percent iodine. Preferably, the catalyst composition comprises alkali metal iodide in the range of from about 0.1 weight percent iodine to about 5 weight percent iodine and, most preferably, in the range of from 0.2 weight percent iodine to 1 weight percent iodine. Generally, the atomic ratio of iodine to alkali metal is in the range of from about 0.5:1 to about 4:1. Preferably, the atomic ratio of iodine to alkali metal is in the range of from about 1:1 to about 3:1. When the alkali metal compound is an alkali metal iodide, it may be used in lieu of the silver.

When the alkali metal compound is an alkali metal fluoride, the catalyst composition comprises alkali metal fluoride in the range of from about 0.03 weight percent fluorine (chemically bound as fluoride) (on a total catalyst composition weight basis) to about 10 weight percent fluorine. Preferably, the catalyst composition comprises alkali metal fluoride in the range of from about 0.1 weight percent fluorine to about 5 weight percent fluorine and, most preferably, in the range of from 0.2 weight percent fluorine to 1 weight percent fluorine. Generally, the atomic ratio of fluorine to alkali metal is in the range of from about 0.5:1 to about 4:1. Preferably, the atomic ratio of fluorine to alkali metal is in the range of from about 1:1 to about 3:1.

The catalyst composition can be prepared by any suitable method(s) or means which results in palladium concentrated in the exterior surface skin of the catalyst composition with a silver metal or compound, or an alkali metal compound, or both silver metal or compound and an alkali metal compound, distributed in the skin or throughout the catalyst composition. Generally, the extent of penetration of the palladium into the skin of the catalyst composition can be controlled by adjustment of the acidity of the palladium-containing solution used in preparing the catalyst composition with an acid such as, for example, hydrochloric acid. For example, if the palladium compound is palladium chloride ($PdCl_2$), hydrochloric acid should be added to the palladium-containing solution containing the palladium chloride to form a ($H_2PdCl_4$) complex. The catalyst composition components (a) palladium and/or at least one palladium oxide, and (b) a catalyst component comprising either silver or an alkali metal compound (preferably potassium fluoride), or both silver and an alkali metal compound, can be deposited onto and/or incorporated into or with the inorganic support material by any suitable means and in any suitable order.

The palladium can be incorporated (e.g., by ion exchange or impregnation) into, onto, or with the metal containing (Ce/Mg) catalyst support. An alternative impregnation utilizes an incipient wetness impregnation technique in which a solution of the incorporating element(s) is added to, and essentially fills the pores of a substrate material completely (such as an inorganic support). The inorganic support can also be sprayed with an impregnating solution comprising a palladium compound. Generally, the concentration of the palladium compound in the impregnating solution is in the range of from about 0.01 mmol/L to about 5 mol/L. Preferably in the range of from about 0.1 mmol/L to about 2 mol/L. Preferably, the solvent of the impregnating solution is water or an alcohol such as ethanol or mixtures thereof. The weight ratio of the impregnating solution comprising a palladium compound to the inorganic support can be any ratio that can produce the catalyst composition comprising palladium in the weight percent ranges disclosed herein.

For example, a catalyst component comprising silver (which includes the element or a compound) or an alkali metal compound, or both silver and an alkali metal compound, can be incorporated into the inorganic support material comprising a metal aluminate (prepared in accordance with the inventive process(es) disclosed herein) by impregnation, followed by impregnation with at least one Pd compound (such as $H_2PdCl_4$ to obtain an impregnated material) drying the impregnated material under a composition drying condition as described herein to obtain a dried material, and then heating (calcining) under a composition calcining condition as described herein to obtain a final catalyst composition of this invention.

In one embodiment, $Ce_2O_3$/MgO/inorganic support (the "metal oxide support") (prepared as disclosed herein) is impregnated with at least one Pd compound (such as $H_2PdCl_4$) to obtain a palladium-impregnated material, drying the impregnated material under a composition drying condition as described herein to obtain a dried material, and then heating (calcining) under a composition calcining condition as described herein to thereby obtain a dried and calcined palladium/metal oxide support composition. The palladium/metal oxide support composition can then be contacted with a solution (preferably aqueous) of at least one silver compound, preferably silver nitrate, (i.e., a silver-containing solution) or an alkali metal compound, preferably potassium fluoride, (i.e., an alkali metal compound-containing solution) followed by drying under a composition drying condition as described herein to obtain a dried material, and then heating (calcining) under a composition calcining condition as described herein to thereby obtain a final catalyst composition of this invention having a concentration of silver or alkali metal in the ranges as disclosed herein.

The palladium/metal oxide support composition can be contacted with a solution (preferably aqueous) of a silver compound (i.e., a silver-containing solution) followed by drying under a composition drying condition as described herein to obtain a dried material, and then heating (calcining) under a composition calcining condition as described herein to thereby obtain a palladium/silver/metal oxide support composition. Such palladium/silver/metal oxide support composition can then be contacted with a solution of an alkali metal compound (i.e., an alkali metal compound-containing solution) followed by drying under a composition drying condition as described herein to obtain a dried material, and then heating (calcining) under a composition calcining condition as described herein to thereby obtain a final catalyst composition of this invention having concentrations of silver and alkali metal in the ranges as disclosed herein.

In addition, an alkali metal compound (or an alkali metal compound-containing solution) can be incorporated (e.g., by impregnation or spraying) onto the metal oxide support before such support is impregnated with a suitable palladium compound (or a palladium-containing solution) and, if desired, with a suitable silver compound (or a silver-containing solution). Alternatively, an alkali metal compound can be incorporated (e.g., by impregnation or spraying) with the metal oxide support simultaneously with or after the impregnation with a suitable palladium compound. When silver is also present in the catalyst composition, an alkali metal compound can be incorporated with the metal oxide support between the palladium and silver impregnation steps or after the impregnation with palladium and silver compounds.

Also for example, a palladium/silver/metal oxide support composition as described herein can be contacted, preferably impregnated, with an aqueous solution of at least one alkali metal hydroxide and/or at least one alkali metal fluoride (preferably KOH and/or KF), followed by drying under a composition drying condition as described herein and calcining under a composition calcining condition as described herein. At least one "wet-reducing" agent (i.e., one or more than one dissolved reducing agent) can also be present during the contacting of the palladium/silver/metal oxide support composition with at least one alkali metal hydroxide and/or at least one alkali metal fluoride. Non-limiting examples of such "wet-reducing" agents are: hydrazine, an alkali metal borohydride, an aldehyde containing 1-6 carbon atoms per molecule such as formaldehyde, a ketone containing 1-6 carbon atoms per molecule, a carboxylic acid containing 1-6 carbon atoms per molecule such as formic acid or ascorbic acid, a reducing sugar containing an aldehyde or alpha-hydroxyketone group such as dextrose, and the like and combinations thereof.

Also for example, a palladium/silver/metal oxide support composition as described herein can be contacted, preferably impregnated, with a non-alkali metal fluoride (preferably selected from the group consisting of HF, $NH_4F$, $(NH_4)HF_2$, and the like and combinations thereof, more preferably $NH_4F$) disclosed herein in any suitable manner. The non-alkali metal fluoride (preferably $NH_4$ F) can be incorporated together with palladium and an alkali metal compound or a suitable silver compound (or palladium and both an alkali metal compound and a suitable silver compound). Alternatively, the non-alkali metal fluoride can be incorporated after the impregnation of the metal oxide support with palladium and an alkali metal compound, or palladium and both an alkali metal compound and a suitable silver compound. After the incorporation of palladium, alkali metal, fluoride (and/or silver) compounds into the support has been completed (as described herein), the thus-obtained material is dried under a composition drying condition as described herein and then calcined under a composition calcining condition as described herein. Optionally, the calcined material can then be reduced with hydrogen gas (preferably at a temperature in the range of from about 30° C. to about 100° C., for a time period in the range of from about 0.5 hour to about 20 hours), so as to reduce oxides of palladium and of silver (if present) to the corresponding metal(s).

Generally, the concentration of a silver compound or an alkali metal compound (preferably an alkali metal fluoride compound) in the contacting solution (preferably aqueous) is in the range of from about 0.01 mmol/L to about 10 mol/L (preferably in the range of from about 0.1 mmol/L to about 3 mol/L). The preferred silver contacting method is by soaking, i.e., essentially completely overfilling the pores and the external surface of the inorganic support material with a silver compound-containing solution. The preferred alkali metal contacting method is "incipient wetness impregnation," i.e., essentially completely filling the pores of the metal oxide support with an alkali metal compound-containing solution (preferably an alkali fluoride-containing solution). Generally, the weight ratio of a silver-containing compound solution or an alkali metal compound-containing solution to the inorganic support material can be any ratio that can produce a catalyst composition having a concentration of silver or alkali metal, or both silver and alkali metal, in the ranges disclosed herein. The impregnated material can then be dried under a composition drying condition as described herein followed by calcining under a composition calcining condition as described herein to obtain the final catalyst composition.

Generally a composition drying condition, as referred to herein, includes a temperature in the range of from about 35° C. to about 160° C., preferably in the range of from about 40° C. to about 155° C. and, most preferably, in the range of from 45° C. to 150° C. Such composition drying condition includes a time period for conducting such drying generally in the range of from about 0.5 hour to about 6 hours, preferably in the range of from about 1 hour to about 5 hours and, most preferably, in the range of from 1.5 hours to 4 hours. Such composition drying condition includes a pressure in the range of from about atmospheric (i.e., about 14.7 pounds per square inch absolute) to about 100 pounds per square inch absolute (psia), preferably about atmospheric.

Generally a composition calcining condition, as referred to herein, includes calcining of the composition either in air or in a non-oxidizing gas atmosphere at a temperature in the range of from about 200° C. to about 800° C., preferably at a temperature in the range of from about 250° C. to about 600° C. and, most preferably, at a temperature in the range of from 350° C. to 550° C. Such composition calcining condition generally includes a time period in the range of from about 0.5 hour to about 40 hours, preferably for a time period in the range of from about 0.75 hour to about 30 hours and, most preferably, for a time period in the range of from 1 hour to 20 hours. Such composition calcining condition generally includes a pressure in the range of from about 7 pounds per square inch absolute (psia) to about 750 psia, preferably in the range of from about 7 psia to about 450 psia and, most preferably, in the range of from 7 psia to 150 psia.

The catalyst composition can be a fresh catalyst composition or it can be a used and oxidatively regenerated catalyst composition. The catalyst composition can have any suitable shape such as spherical, cylindrical, trilobal, or combinations thereof. The preferred shape is either spherical or cylindrical. The particle size of the supported catalyst composition of the invention is generally in the range of from about 0.5 millimeters (mm) to about 10 mm, preferably in the range of from about 1 mm to about 8 mm and, most preferably, in the range of from 1 mm to 6 mm. Generally, the surface area of the catalyst composition is in the range of from about 1 $m^2/g$ (measured by the Brunauer, Emmett, Teller method, i.e., BET method) to about 200 $m^2/g$, preferably in the range of from about 1 $m^2/g$ to about 150 $m^2/g$, and more preferably in the range of from about 3 $m^2/g$ to about 125 $m^2/g$.

According to another embodiment of the invention, a hydrogenation process is provided. The inventive hydrogenation process comprises contacting a hydrocarbon-containing fluid which comprises one or more highly unsaturated hydrocarbon(s) such as an aromatic hydrocarbon(s), alkyne(s), and/or diolefin(s) with the inventive unsupported or supported catalyst composition comprising cerium, magnesium, and optionally an inorganic support, in the presence of hydrogen in a hydrogenation zone under a hydrogenation condition to hydrogenate such one or more highly unsaturated hydrocarbon(s) to a less unsaturated hydrocarbon.

According to yet another embodiment of the invention, an isomerization process is provided. The inventive isomerization process comprises contacting a hydrocarbon-containing fluid which comprises one or more highly unsaturated hydrocarbon(s) such as an alkyne(s) and/or a diolefin(s) with the inventive unsupported or supported catalyst composition comprising cerium, magnesium, and optionally an inorganic support as disclosed herein, in the presence of hydrogen in an isomerization zone under an isomerization condition to isomerize such one or more highly unsaturated hydrocarbon(s), such as a diolefin, to another highly unsaturated hydrocarbon(s), such as an alkyne(s) which, if desired, can then be more efficiently hydrogenated to a less unsaturated hydrocarbon(s) according to the hydrogenation process.

The highly unsaturated hydrocarbon(s) is present in the hydrocarbon-containing fluid as an impurity generally at a level found in typical commercial feed streams. The highly unsaturated hydrocarbon(s) is present in the hydrocarbon-containing fluid generally in the range of from about 1 part by weight highly unsaturated hydrocarbon(s) per billion parts by weight hydrocarbon-containing fluid (i.e., about 1 ppb) to about 50 parts by weight highly unsaturated hydrocarbon(s) per 500 parts by weight hydrocarbon-containing fluid (i.e., about 10 weight percent), typically at a level in the range of from about 10 ppb to about 5 weight percent and, most typically, at a level in the range of from 100 ppb to 1 weight percent.

Hydrogen can be present either in the hydrocarbon-containing fluid or in a hydrogen-containing fluid that is mixed with the hydrocarbon-containing fluid before contacting with a catalyst composition of the invention. If a hydrogen-containing fluid is used, it can be a substantially pure hydrogen or any fluid containing a sufficient concentration of hydrogen to effect the hydrogenation and/or isomerization disclosed herein. It can also contain other gases such as, for example, nitrogen, methane, carbon monoxide, carbon dioxide, steam, or combinations thereof so long as the hydrogen-containing fluid contains a sufficient concentration of hydrogen to effect the hydrogenation and/or isomerization disclosed herein.

Optionally, the catalyst composition can be first treated, prior to the hydrogenation and/or isomerization disclosed herein, with a hydrogen-containing fluid to activate the catalyst composition. Such reductive, or activation, treatment can be carried out at a temperature generally in the range of from about 20° C. to about 200° C., preferably in the range of from about 25° C. to about 150° C. and, most preferably, in the range of from 30° C. to 125° C. for a time period in the range of from about 1 minute to about 30 hours, preferably in the range of from about 0.5 hour to about 25 hours and, most preferably, in the range of from 1 hour to 20 hours at a pressure generally in the range of from about 1 pound per square inch absolute to about 1,000 pounds per square inch absolute (psia), preferably in the range of from about 14.7 psia to about 500 psia and, most preferably, in the range of from 60 psia to 200 psia. When this optional reductive treatment is not carried out, the hydrogen gas or hydrocarbon present in the reaction medium accomplishes this reduction during the initial phase of the selective hydrogenation and/or isomerization process(es).

The hydrocarbon-containing fluid can also comprise at least one less unsaturated hydrocarbon(s) such as a monoolefin(s) and one or more saturated hydrocarbon(s) such as an alkane(s). These additional hydrocarbons can be present in the hydrocarbon-containing fluid at a level in the range of from about 0.001 weight percent to about 99.999 weight percent.

Examples of suitable alkynes include, but are not limited to, acetylene, methyl acetylene (also referred to as propyne), 1-butyne, 2-butyne, 1-pentyne, 2-pentyne, 3-methyl-1-butyne, 1-hexyne, 1-heptyne, 1-octyne, 1-nonyne, 1-decyne, and the like and combinations thereof. The presently preferred alkynes are acetylene and methyl acetylene.

According to the hydrogenation process, the alkynes are primarily hydrogenated to the corresponding alkenes. Preferably, acetylene is primarily hydrogenated to ethylene; methyl acetylene is primarily hydrogenated to propylene; and the butynes are primarily hydrogenated to the corresponding butenes (e.g., 1-butene, 2-butenes).

Examples of suitable diolefins include those containing in the range of from 3 carbon atoms per molecule to about 12 carbon atoms per molecule. Such diolefins include, but are not limited to, propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, and the like and combinations thereof.

Presently preferred diolefins are propadiene, 1,2-butadiene, 1,3-butadiene, pentadienes (such as 1,3-pentadiene, 1,4-pentadiene, isoprene), cyclopentadienes (such as 1,3-cyclopentadiene) and dicyclopentadiene (also known as tricyclo [5.2.1]2,6-deca-3,8-diene).

According to a hydrogenation process of the invention, the diolefins disclosed herein are preferably hydrogenated to their corresponding monoolefins containing the same number of carbon atoms per molecule as the diolefins. For example, propadiene is hydrogenated to propylene, 1,2-butadiene and 1,3-butadiene are hydrogenated to 1-butene and 2-butene, 1,3-pentadiene and 1,4-pentadiene are hydrogenated to 1-pentene and 2-pentene, isoprene is hydrogenated to methyl-1-pentenes and methyl-2-pentenes, and 1,3-cyclopentadiene is hydrogenated to cyclopentene.

According to an isomerization process of the invention, the diolefins disclosed herein are preferably isomerized to their corresponding alkyne(s) containing the same number of carbon atoms per molecule as the diolefins. Preferably, propadiene is isomerized to methyl acetylene, 1,2-butadiene and 1,3-butadiene are isomerized to 1-butyne and 2-butyne, 1,3-pentadiene and 1,4-pentadiene are isomerized to 1-pentyne, 2-pentyne, 1,3-hexadiene is isomerized to 1,3-hexyne, and 1,3-heptadiene is isomerized to 1-heptyne.

Examples of suitable aromatic hydrocarbons include, but are not limited to, benzene, toluene, ethylbenzene, styrene, xylenes, and the like and combinations thereof.

Examples of suitable monoolefins include, but are not limited to, ethylene, propylene, 1-butene, 2-butene, isobutylene, 1-pentene, 2-pentene, methyl-1-butenes (such as 2-methyl-1-butene), methyl-2-butenes (such as 2-methyl-2-butene), 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and the like and combinations thereof.

Examples of suitable saturated hydrocarbons include, but are not limited to, methane, ethane, propane, butane, methylpropane, methylbutane, dimethylbutane, pentanes, hexanes, and the like and combinations thereof.

Furthermore, the hydrocarbon-containing fluid can contain in the range of from about 0.001 weight percent hydrogen to about 5 weight percent hydrogen, and up to 5,000 parts per million by volume (ppmv) of carbon monoxide.

The hydrocarbon-containing fluid disclosed herein may contain an impurity at a level which does not significantly interfere with the hydrogenation process of a highly unsaturated hydrocarbon to a less unsaturated hydrocarbon as disclosed herein and/or an isomerization process of a highly unsaturated hydrocarbon to another highly unsaturated hydrocarbon as disclosed herein. The term "impurity" as used herein denotes any component in a hydrocarbon-containing fluid that is not a major component. Examples of impurities other than an alkyne or a diolefin include, but are not limited to carbon monoxide, hydrogen sulfide ($H_2S$), carbonyl sulfide (COS), carbon disulfide ($CS_2$), mercaptans (RSH), organic sulfides (RSR), organic disulfides (RSSR), thiophene, organic trisulfides, organic tetrasulfides, organic polysulfides, and the like and combinations thereof, wherein each R can be an alkyl or cycloalkyl or aryl group containing 1 carbon atom to about 15 carbon atoms, preferably 1 carbon atom to 10 carbon atoms. It is within the scope of this invention to have additional compounds (such as water, alcohols, ethers, aldehydes, ketones, carboxylic acids, esters, other oxygenated compounds, and the like and combinations thereof) present in the hydrocarbon-containing fluid, as long as they do not significantly interfere with the hydrogenation process of a highly unsaturated hydrocarbon to a less unsaturated hydrocarbon as disclosed herein and/or an isomerization process of a highly unsaturated hydrocarbon to another highly unsaturated hydrocarbon as disclosed herein.

According to one embodiment of the hydrogenation process of the invention, the hydrocarbon-containing fluid comprises greater than about 85 weight percent (wt %) propylene based on the total weight of the hydrocarbon-containing fluid, preferably greater than about 90 weight percent propylene, and more preferably greater than about 95 weight percent propylene and an amount of methyl acetylene in the range of from about 0.1 to about 15 weight percent methyl acetylene based on the total weight of the hydrocarbon-containing fluid, preferably in the range of from about 0.1 to about 10 weight percent methyl acetylene, and more preferably in the range of from about 0.1 to about 5 weight percent methyl acetylene, and the rest of the hydrocarbon-containing fluid comprising trace amounts of methane, ethane, and ethylene.

According to an embodiment of the hydrogenation process of the invention, the hydrocarbon-containing fluid comprises greater than about 50 weight percent (wt %) ethylene based on the total weight of the hydrocarbon-containing fluid, preferably greater than about 60 weight percent ethylene, and more preferably greater than about 70 weight percent ethylene.

According to another embodiment of the hydrogenation process of the invention, the total weight of highly unsaturated hydrocarbon converted, i.e., hydrogenated, to other compounds as a percentage of the total weight of the highly unsaturated hydrocarbon in the hydrocarbon-containing fluid is generally greater than about 50 percent, preferably greater than about 80 percent, and more preferably greater than about 85 percent. It is preferred for a substantial amount of the methyl acetylene in the hydrocarbon-containing fluid to be converted, i.e., hydrogenated, to propylene, as opposed to other compounds. Generally, the weight of methyl acetylene converted to propylene as a percentage of the weight of the total methyl acetylene converted is at least about 45 percent, preferably at least about 55 percent, and more preferably at least about 65 percent.

According to one embodiment of the isomerization process of the invention, a preferred hydrocarbon-containing fluid comprises greater than about 85 weight percent propylene based on the total weight of the hydrocarbon-containing fluid, preferably greater than about 90 weight percent propylene, and more preferably greater than about 95 weight percent propylene and an amount of propadiene in the range of from about 0.1 to about 2 weight percent propadiene based on the total weight of the hydrocarbon-containing fluid, preferably in the range of from about 0.1 to about 1 weight percent propadiene, and more preferably in the range of from 0.1 to 0.5 weight percent propadiene. The hydrocarbon-containing fluid further comprises methyl acetylene in an amount in the range of from about 0.1 to about 2 weight percent methyl acetylene based on the total weight of the hydrocarbon-containing fluid, preferably in the range of from about 0.1 to about 1 weight percent methyl acetylene, and more preferably in the range of from 0.1 to 0.5 weight percent methyl acetylene.

According to another embodiment of the isomerization process of the invention, the weight of propadiene converted, i.e., isomerized, to other compounds as a percentage of the total weight of the propadiene in the hydrocarbon-containing fluid is generally greater than about 50 percent, preferably greater than about 60 percent, and more preferably greater than about 70 percent. It is preferred for a substantial amount of the propadiene in the hydrocarbon-containing fluid to be converted, i.e., isomerized, to methyl acetylene, as opposed to other compounds. Generally, the weight of propadiene converted to methyl acetylene as a percentage of the weight of the total propadiene converted is greater than about 20 percent, preferably greater than about 40 percent, and more preferably greater than about 50 percent.

The hydrogenation process of the invention is generally carried out by contacting a hydrocarbon-containing fluid comprising at least one highly unsaturated hydrocarbon, in the presence of hydrogen, with a supported and/or unsupported catalyst composition of the invention under a hydrogenation condition. The hydrocarbon-containing fluid can be contacted by any suitable manner with the supported and/or unsupported catalyst composition that is contained within a hydrogenation zone. Such hydrogenation zone can comprise, for example, a reactor vessel.

The isomerization process of the invention is generally carried out by contacting a hydrocarbon-containing fluid comprising at least one highly unsaturated hydrocarbon, in the presence of hydrogen, with a supported and/or unsupported catalyst composition of the invention comprising cerium, magnesium, and an inorganic support, preferably alumina, under an isomerization condition. The hydrocarbon-containing fluid can be contacted by any suitable manner with the supported catalyst composition that is contained within an isomerization zone. Such isomerization zone can comprise, for example, a reactor vessel.

The hydrogenation and isomerization process(es) of the invention can be conducted separately or simultaneously in separate zones or in the same zone. For example, a hydrogenation process of the invention can be conducted using a supported and/or unsupported catalyst composition of the invention in a hydrogenation zone. Also for example, an isomerization process of the invention can be conducted using a supported catalyst composition of the invention in an isomerization zone. Also for example, a hydrogenation process of the invention and an isomerization process of the invention can be conducted simultaneously in the same zone using a supported and/or unsupported catalyst composition of the invention to conduct the hydrogenation and a supported catalyst composition of the invention to conduct the isomerization. The hydrogenation zone and the isomerization zone can be the same zone, can be zones in series, can be zones in parallel, and the like and combinations thereof.

The contacting step, of contacting a hydrocarbon-containing fluid with the catalyst composition of the invention, can be operated as a batch process step or, preferably, as a continuous process step. In the latter operation, a solid or fixed catalyst bed, a moving catalyst bed, or a fluidized catalyst bed can be employed. Preferably, a fixed catalyst bed is employed. Any of these operational modes have advantages and disadvantages, and those skilled in the art can select the one most suitable for a particular hydrocarbon-containing fluid and catalyst composition.

The contacting step of the hydrogenation process as disclosed herein is preferably carried out within a hydrogenation zone, wherein is contained a supported and/or unsupported catalyst composition of the invention, and under a hydrogenation condition that suitably promotes the hydrogenation process of a highly unsaturated hydrocarbon to a less unsaturated hydrocarbon as disclosed herein. Such hydrogenation condition should be such as to avoid significant hydrogenation of a less unsaturated hydrocarbon(s) being initially present in the hydrocarbon-containing fluid to a saturated hydrocarbon(s) such as an alkane(s) or cycloalkane(s).

The contacting step of the isomerization process as disclosed herein is carried out within an isomerization zone, containing a supported catalyst composition of the invention, and under an isomerization condition that suitably promotes the isomerization process of a highly unsaturated hydrocarbon as disclosed herein. Such isomerization condition should be such as to avoid significant isomerization of a less unsaturated hydrocarbon(s) being initially present in the hydrocarbon-containing fluid.

Generally, the hydrogenation process of the invention comprises the presence of hydrogen, preferably hydrogen gas, in an amount in the range of from about 0.1 mole of hydrogen employed for each mole of highly unsaturated hydrocarbon present in the hydrocarbon-containing fluid to about 1,000 moles of hydrogen employed for each mole of highly unsaturated hydrocarbon present in the hydrocarbon-containing fluid. Preferably, a hydrogenation process of the invention comprises the presence of hydrogen, preferably hydrogen gas, in an amount in the range of from about 0.5 mole to about 500 moles of hydrogen employed for each mole of highly unsaturated hydrocarbon present in the hydrocarbon-containing fluid and, more preferably, in the range of from 0.7 mole to 200 moles of hydrogen employed for each mole of highly unsaturated hydrocarbon present in the hydrocarbon-containing fluid.

Generally, the hydrogenation process of the invention proceeds at a temperature and a pressure necessary for a hydrogenation process of the invention depending largely upon the activity of the supported and/or unsupported catalyst composition, the hydrocarbon-containing fluid, and the desired extent of hydrogenation. Generally, such temperature is in the range of from about 10° C. to about 300° C., preferably in the range of from about 20° C. to about 250° C. and, more preferably, in the range of from 20° C. to 200° C. Suitable pressures are generally in the range of from about 15 pounds per square inch gauge (psig) to about 2,000 psig, preferably in the range of from about 50 psig to about 1,500 psig and, more preferably, in the range of from 100 psig to 1,000 psig.

Such hydrogenation process conditions further includes the flow rate at which the hydrocarbon-containing fluid is charged (i.e., the charge rate of hydrocarbon-containing fluid) to a hydrogenation zone of the invention. The flow rate is such as to provide a gas hourly space velocity ("GHSV") of at least about 1 liters of hydrocarbon-containing fluid per liter of catalyst per hour (units of $hr^{-1}$). The term "gas hourly space velocity", as used herein, shall mean the numerical ratio of the rate at which a hydrocarbon-containing fluid is charged to a hydrogenation and/or isomerization zone of the invention in liters per hour at standard condition of temperature and pressure ("STP") divided by the liters of catalyst composition contained in such hydrogenation and/or isomerization zone to which the hydrocarbon-containing fluid is charged. Typically, such hydrogenation condition comprises a gas hourly space velocity of the hydrocarbon-containing fluid in the range of from about 1 to about 50,000 liters of hydrocarbon-containing fluid per liter of catalyst per hour ($hr^{-1}$), preferably in the range of from about 750 $hr^{-1}$ to about 40,000 $hr^{-1}$ and, most preferably, in the range of from 1,000 to about 30,000 $hr^{-1}$.

Generally, the isomerization process of the invention comprises the presence of hydrogen, preferably hydrogen gas, in an amount in the range of from about 0.1 mole of hydrogen employed for each mole of highly unsaturated hydrocarbon present in the hydrocarbon-containing fluid to about 1,000 moles of hydrogen employed for each mole of highly unsaturated hydrocarbon present in the hydrocarbon-containing fluid. Preferably, an isomerization process of the invention comprises the presence of hydrogen, preferably hydrogen gas, in an amount in the range of from about 0.5 mole to about 500 moles of hydrogen employed for each mole of highly unsaturated hydrocarbon present in the hydrocarbon-containing fluid and, more preferably, in the range of from 0.7 mole to 200 moles of hydrogen employed for each mole of highly unsaturated hydrocarbon present in the hydrocarbon-containing fluid.

Generally, the isomerization process of the invention proceeds at a temperature and a pressure necessary for an isomerization process of the invention depending largely upon the activity of the supported catalyst composition of the invention, the hydrocarbon-containing fluid, and the desired extent of isomerization. Generally, such temperature is in the range of from about 10° C. to about 300° C., preferably in the range of from about 20° C. to about 250° C. and, more preferably, in the range of from 20° C. to 200° C. Suitable pressures are generally in the range of from about 15 pounds per square inch gauge (psig) to about 2,000 psig, preferably in the range of from about 50 psig to about 1,500 psig and, more preferably, in the range of from 100 psig to 1,000 psig.

The isomerization process conditions of the invention further includes the flow rate at which the hydrocarbon-containing fluid is charged (i.e., the charge rate of hydrocarbon-containing fluid) to an isomerization zone of the invention. The flow rate is such as to provide a gas hourly space velocity generally at least about one $hr^{-1}$. Typically, the gas hourly space velocity of the hydrocarbon-containing fluid will be in the range of from about 1 to about 50,000 liters of hydrocarbon-containing fluid per liter of catalyst per hour ($hr^{-1}$), preferably in the range of from about 750 to about 40,000 $hr^{-1}$ and, most preferably, in the range of from 1,000 to about 30,000 $hr^{-1}$.

If it is desired to regenerate a supported and/or unsupported catalyst composition of the invention after prolonged use in a hydrogenation process and/or isomerization process of the invention, the regeneration can be accomplished by calcining the supported and/or unsupported catalyst composition in an oxidizing atmosphere such as in air at a temperature that does not exceed about 700° C. to burn off carbonaceous deposits.

The following examples are presented to further illustrate the invention and are not to be construed as unduly limiting the scope of the invention. In the Examples below and their associated tables, Table I, $C_1$ denotes methane; $C_2$ denotes ethane; $C_2^=$ denotes ethylene; $C_3$ denotes propane; $C_3^=$ denotes propylene; $C_4$s denotes hydrocarbons containing 4 carbon atoms such as butane, butene, and butadiene; PD denotes propadiene; MA denotes methyl acetylene; and $C_6^+$ denotes hydrocarbons containing 6 or more carbon atoms. In Examples 11 and 13 below and their associated tables, two temperatures were measured. The first temperature, $T_1$, is the temperature at which the acetylene concentration has dropped to less than 20 parts per million by weight (ppm). It is desirable to operate at or above $T_1$ to minimize the amount of highly unsaturated hydrocarbons in the product. The second temperature, $T_2$, is the temperature at which the ethane production is no more than 3 wt %. It is desirable to operate below $T_2$ to minimize the loss of less unsaturated hydrocarbon product by conversion into saturated hydrocarbon. $\Delta T$, the difference between $T_2$ and $T_1$, which is the effective operating temperature range of the catalyst, is also noted.

Example 1

Preparation of Catalyst A

Catalyst A was an unsupported catalyst composition comprising cerium and magnesium prepared substantially in accordance with the procedure disclosed in the article entitled "Ortho-Selective Methylation of Phenol Catalyzed by $CeO_2$—MgO Prepared by Citrate Process" in the Journal of Catalysis, 178 (1998), pages 264-274. 0.89 mole of magnesium nitrate hexahydrate was mixed with 0.11 mole cerium nitrate hexahydrate and 1 mole citric acid monohydrate in a 1 liter round bottom flask which was placed in a rotary evaporator. This mixture was heated at 80° C. for about 16 hours. Heating was discontinued and the flask was then rotated under vacuum for about 16 hours. The flask was then placed in a drying oven at 120° C. for about 30 minutes. The flask was then transferred to a muffle furnace and slowly heated to 130° C. over a 1-hour period. The temperature was then increased to 160° C. and maintained at 160° C. for 30 minutes and then increased to 190° C. and maintained at 190° C. for 30 minutes. After 30 minutes at 190° C., $NO_x$ emission was observed and the furnace was turned off. The flask was then allowed to cool. The resulting material in the flask was then scraped from the flask and transferred to a crucible. The crucible was then heated in air at a rate of 5° C. per minute to a temperature of 150° C. and then maintained at 150° C. for 1 hour. The temperature was then increased at 10° C. per minute to a temperature of 520° C. and maintained at 520° C. for 5 hours. The crucible was then allowed to cool for about 16 hours. 46.1 grams of the resulting unsupported catalyst composition, Catalyst A, was obtained. Catalyst A was subjected to BET analysis and found to have a surface area of about 148 $m^2/g$, a pore volume of about 0.31 ml/g, and an average pore diameter of about 83 angstroms.

Example 2

Preparation of Catalyst B

Catalyst B was a supported catalyst comprising cerium, magnesium, and alumina. 50 grams of commercially available delta alumina (provided by United Catalyst Inc., Louisville, Ky. obtained as precalcined tablets having a surface area of 20 m²/g in the form of 4 mm×4 mm tablets) was placed in a 250 mL beaker in a drying oven at 120° C. 16 grams of magnesium nitrate hexahydrate, 2.7 grams of cerium nitrate hexahydrate, 14.5 grams of citric acid monohydrate, and about 14 mL distilled water were placed in a 250 mL beaker in a drying oven at 120° C. and heated for a time period of about 15 to about 30 minutes. The mixture melted, turned pale yellow, and began to emit $NO_x$ gas. Under a ventilating hood, the molten mixture was slowly added to the pre-heated delta alumina, which was being stirred and heated on a hot plate during such addition of the molten mixture. Distilled water was periodically added during such addition. The resulting cerium and magnesium impregnated delta alumina was then heated and stirred for a time period of about 60 to about 120 minutes. After cooling for about 1 hour, the impregnated delta alumina was loaded into a quartz calcining tube and heated at about 160° C. for about 1.5 hours. The temperature was then increased to about 240° C. and maintained at about 240° C. for about 0.5 hour. The temperature was then increased to about 555° C. and maintained at 555° C. for about 6 hours and then allowed to cool at room temperature. The resulting supported catalyst composition contained about 3 weight percent magnesium, 1.7 weight percent cerium, with a molar ratio of Mg:Ce of about 10:1.

Example 3

Isomerization Performance of Catalyst A

About 17 cc of Catalyst A were loaded into a water-jacketed stainless steel reactor (0.5 inch inner diameter; 18 inches long). Thermocouples were inserted into a thermowell which ran through the center and coaxial with the reactor. The reactor was heated in a three-zone furnace. The catalyst was then treated with hydrogen gas flowing at about 50 cc/min at a temperature of about 204° C. for about 3 hours. The catalyst was then allowed to cool for about 16 hours. Thereafter, a hydrocarbon-containing fluid having a composition as disclosed in Table I was continuously introduced into the reactor at a pressure of 200 psig at the temperatures disclosed in Table I. The catalyst was exposed to each temperature for about 10 to 15 minutes. The product stream was analyzed by gas chromatography using both Flame Ionization (FID) and Thermal Conductivity (TCD) detection. The results from Example II are shown in Table I. The numbers disclosed in Table I are mole percent unless otherwise noted.

TABLE I

Isomerization Performance of Catalyst A (Unsupported $CeO_2$—MgO)

|  | Feed Analysis | 22° C. | 41° C. | 76° C. | 97° C. | 125° C. | 158° C. |
|---|---|---|---|---|---|---|---|
| | | FID | | | | | |
| $C_6^+$ | 0.0 | 0 | 0 | 0 | 0 | 0 | 0 |
| $C_1$ | 20.2 | 20.1 | 20.1 | 20.1 | 20.2 | 20.1 | 20.1 |
| $C_2 + C_2^=$ | 55.4 | 56.0 | 56.1 | 55.0 | 55.2 | 56.0 | 56.0 |
| $C_3^+$ Acetylene | 0.4 | 0.36 | 0.4 | 0.4 | 0.4 | 0.4 | 0.3 |
| $C_3^=$ | 23.2 | 22.7 | 22.7 | 22.7 | 22.7 | 22.7 | 22.7 |
| Propadiene (PD) | 0.4 | 0.4 | 0.4 | 0.4 | 0.4 | 0.4 | 0.4 |
| Methyl acetylene (MA) | 0.4 | 0.4 | 0.4 | 0.4 | 0.4 | 0.4 | 0.4 |
| $C_4$s | 0 | 0 | 0 | 0 | 0 | 0 | 0 |
| PD + MA | 0.8 | 0.8 | 0.8 | 0.8 | 0.8 | 0.8 | 0.8 |
| | | TCD | | | | | |
| $C_2^=$ | 69.8 | 69.9 | 69.9 | 69.9 | 69.8 | 69.8 | 69.8 |
| $C_2$ | 0 | 0.1 | 0.1 | 0.1 | 0.1 | 0.1 | 0.1 |
| Acetylene | 0.6 | 0.6 | 0.6 | 0.6 | 0.6 | 0.6 | 0.5 |
| $C_1$ | 29.6 | 29.5 | 29.4 | 29.4 | 29.5 | 29.5 | 29.6 |
| | | Conversion | | | | | |
| % PD conversion | — | 0.3 | 1.0 | 0.3 | 0.8 | 0.8 | 3.9 |
| % MA conversion | — | −1.2 | −1.7 | 1.0 | 0.7 | 1.5 | 8.0 |
| % MAPD conversion | — | −0.5 | −0.4 | 0.6 | 0.8 | 1.1 | 6.0 |

Feed flow rate: 700 cc/min; H2 flow rate: 200 cc/min

The data in Table I show that catalyst composition A exhibited no significant propadiene conversion activity when the feed comprised about 70% ethylene by TCD and small amounts of propadiene and methyl acetylene.

TABLE II

Isomerization Performance of Catalyst B (Supported $CeO_2$—MgO)

|  | Feed Analysis | 42° C. | 74° C. | 96° C. | 22° C. |
|---|---|---|---|---|---|
| | | FID | | | |
| $C_6^+$ | 0.0 | 0 | 0 | 0 | 0 |
| $C_1$ | 20.2 | 20.1 | 20.1 | 20.1 | 20.2 |
| $C_2 + C_2^=$ | 55.4 | 56.0 | 55.9 | 55.9 | 55.9 |
| $C_3^+$Acetylene | 0.4 | 0.4 | 0.4 | 0.4 | 0.4 |
| $C_3^=$ | 23.2 | 22.7 | 22.7 | 22.8 | 22.7 |
| Propadiene (PD) | 0.4 | 0.1 | 0.1 | 0.1 | 0.2 |
| Methyl acetylene (MA) | 0.4 | 0.7 | 0.7 | 0.7 | 0.7 |
| $C_4$s | 0 | 0 | 0 | 0 | 0 |
| PD + MA | 0.8 | 0.8 | 0.8 | 0.8 | 0.8 |

TABLE II-continued

Isomerization Performance of Catalyst B (Supported $CeO_2$—MgO)

| | Feed Analysis | Reactor Temperature | | | |
|---|---|---|---|---|---|
| | | 42° C. | 74° C. | 96° C. | 22° C. |
| | | TCD | | | |
| $C_2^=$ | 69.8 | 69.9 | 69.8 | 69.8 | 69.9 |
| $C_2$ | 0 | 0.0 | 0.1 | 0.1 | 0.04 |
| Acetylene | 0.6 | 0.6 | 0.6 | 0.6 | 0.6 |
| $C_1$ | 29.6 | 29.5 | 29.5 | 29.5 | 29.5 |
| | | Conversion | | | |
| % PD conversion | — | 76.0 | 74.4 | 72.9 | 62.5 |
| % MA conversion | — | −73.1 | −69.4 | −68.2 | −59.5 |
| % MAPD conversion | — | −0.9 | 0.3 | 0.1 | −0.4 |
| $C_2^=$ selectivity, % | — | −3360 | 39.0 | 92.8 | −4266.7 |
| $C_2^=$ | — | 55.9 | 55.9 | 55.9 | 55.9 |
| $C_2$ make | — | 0.04 | 0.08 | 0.08 | 0.04 |

Feed flow rate: 700 cc/min;
H2 flow rate: 200 cc/min

Example 4

Isomerization Performance of Catalyst B

About 20 cc of Catalyst B were loaded into a water jacketed stainless steel reactor (0.5 inch inner diameter; 18 inches long). Thermocouples were inserted into a thermowell which ran through the center and coaxial with the reactor. The reactor was heated in a three-zone furnace. The catalyst was then treated with hydrogen gas flowing at about 50 cc/min at a temperature of about 204° C. for about 3 hours. The catalyst was then allowed to cool overnight for about 16 hours. Thereafter, a hydrocarbon-containing fluid having a composition as disclosed in Table II was continuously introduced into the reactor at a pressure of 200 psig at the temperatures disclosed in Table II. The catalyst was exposed to each temperature for about 10 to 15 minutes. The product stream was the analyzed by gas chromatography using both FID and TCD detection. The results from Example III are shown in Table II. The numbers disclosed in Table II are mole percent unless otherwise noted.

The data in Table II illustrates that Catalyst B converted about 76 percent propadiene to methyl acetylene at 42° C.

Example 5

Hydrogenation Performance of Catalyst A

About 20 cc of Catalyst A were loaded into a water-jacketed stainless steel reactor (0.5 inch inner diameter; 18 inches long). Thermocouples were inserted into a thermowell that ran coaxially through the center of the reactor. The reactor was heated with a three-zone furnace. The catalyst was then treated with hydrogen gas flowing at 100 cc/min at a temperature of about 202° C. for about 1 hour. Thereafter, a hydrocarbon-containing fluid having a composition as disclosed in Table IV was continuously introduced into the reactor at temperatures, pressures, and hydrogen flow rates as disclosed in Table III. The product stream was analyzed by gas chromatography using both FID and TCD detection. The results obtained are disclosed in Table IV. The numbers disclosed in Table IV are mole percent unless otherwise noted.

TABLE III

| Sample # | Top Temperature (° C.) | Middle Temperature (° C.) | Bottom Temperature (° C.) | Pressure (psig) | Hydrogen Flow Rate (cc/min) |
|---|---|---|---|---|---|
| 1 | 100 | 99 | 96 | 220 | 25 |
| 2 | 125 | 126 | 119 | 220 | 25 |
| 3 | 157 | 157 | 153 | 220 | 50 |
| 4 | 156 | 155 | 150 | 420 | 50 |
| 5 | 166 | 166 | 161 | 614 | 100 |
| 6 | 176 | 176 | 171 | 614 | 100 |
| 7 | 189 | 189 | 182 | 614 | 100 |

TABLE IV

Hydrogenation Performance of Catalyst A (Unsupported $CeO_2$—MgO)

| | Feed Analysis | Sample | | | | | | |
|---|---|---|---|---|---|---|---|---|
| | | #1 | #2 | #3 | #4 | #5 | #6 | #7 |
| | | FID | | | | | | |
| $C_6^+$ | 0.0 | 0.0 | 0.0 | 0.1 | 0.2 | 0.2 | 0.2 | 0.2 |
| $C_3$ | 0.4 | 0.3 | 0.3 | 0.4 | 0.5 | 0.8 | 0.7 | 0.9 |
| $C_3^=$ | 23.2 | 97.1 | 97.2 | 97.7 | 98.2 | 98.6 | 98.7 | 98.7 |
| Propadiene (PD) | 0.4 | 0.2 | 0.2 | 0.2 | 0.1 | 0.1 | 0.1 | 0.0 |
| Methyl acetylene (MA) | 0.4 | 2.4 | 2.2 | 1.6 | 1.0 | 0.4 | 0.4 | 0.1 |
| | | Conversion and Selectivity | | | | | | |
| % MA conversion | — | 11.1 | 17.5 | 39.9 | 62.1 | 86.7 | 86.4 | 95.6 |
| % $C_3$ Selectivity | — | 3.7 | 3.9 | 7.9 | 12.9 | 22.1 | 18.7 | 24.3 |
| % PD Selectivity | — | 58.8 | 44.3 | 15.5 | 7.5 | 2.4 | 2.8 | 1.1 |
| % $C_6^+$ Selectivity | — | 2.4 | 5.6 | 7.8 | 9.3 | 6.3 | 6.6 | 5.8 |
| % $C_3^=$ Selectivity | — | 35.4 | 46.5 | 68.9 | 70.2 | 69.2 | 71.9 | 68.7 |

While the isomerization activity was not evaluated in this trial, the data in Table IV demonstrate that Catalyst A does selectively hydrogenate methyl acetylene with about 70 percent selectivity to propylene at about 86 percent methyl acetylene conversion (samples #5 and #6).

The hydrocarbon-containing fluid of the hydrogenation process(es) of this invention can also comprise one or more less unsaturated hydrocarbon(s) such as a monoolefin(s) and one or more saturated hydrocarbon(s) such as an alkane(s). These additional hydrocarbons can be present in the hydrocarbon-containing fluid at a level in the range of from about 0.001 weight percent to about 99.999 weight percent.

Example 6

Preparation of $Ce_2O_3/MgO/\delta$-$Al_2O_3$ Catalyst Support Samples C-F 50 g of $\delta$-$Al_2O_3$ oil-drop spheres were weighed into four separate 250 ml beakers. The beakers were placed in a drying oven at 120° C. $Ce(NO_3)_3 \cdot 6H_2O$, $Mg(NO_3)_2 \cdot 6H_2O$, distilled $H_2O$, and citric acid monohydrate were each added to four separate containers labeled C, D, E, & F. The amounts of the components in each sample is shown in Table V. Samples C-E were placed in the drying oven at a temperature of about 120° C. After about 15-30 minutes, the mixture of Sample C-E melted and/or dissolved, turned pale yellow and began to emit $NO_x$ gas. Each of Samples C-E mixture was then slowly added with constant stirring, to one of the beakers of preheated $\delta$-$Al_2O_3$, resulting in "impregnated $Al_2O_3$ samples." The impregnated alumina samples C-E were heated and stirred from about 60-120 minutes for each sample. For sample F, the $Mg(NO_3)_2 \cdot 6H_2O$ was dissolved in distilled water and dropwise added to a cooled beaker of the $\delta$-$Al_2O_3$. Each of Samples C-F were loaded into quartz calcining tubes and heated as outlined below. Samples C-E were heated together in the same furnace. Sample F was heated separately.

Calcinations were performed in an air purge according to the schedule below.

| Samples C-E | | Sample F | |
|---|---|---|---|
| Time | Temperature | Time | Temperature |
|  |  | 2 hr. | 120° C. |
| 1.5 hr. | 160° C. | 16 hr. | 240° C. |
| 0.5 hr. | 240° C. | 2 hr. | 440° C. |
| 6.0 hr. | 555° C. | 4 hr. | 545° C. |

Samples C-F were allowed to cool to room temperature. Sample E appeared to contain some residual carbon, and was thus heated to 600° C. for an additional two hours. The final compositions of samples C-F are given in Table V:

TABLE V

| Sample # | $Mg(NO_3)_2 \cdot 6H_2O$ (grams) | $Ce(NO_3)_3 \cdot 6H_2O$ (grams) | Distilled $H_2O$ (grams) | Citric Acid Monohydrate (grams) | Mg: Ce (molar) | Mg (wt %) | Ce (wt %) |
|---|---|---|---|---|---|---|---|
| C | 8.0 | 1.3 | 10 | 7.3 | 10.1 | 1.5 | 0.9 |
| D | 16.0 | 5.6 | 7.8 | 14.5 | 4.8 | 3.0 | 3.6 |
| E | 16.0 | 1.4 | 7.7 | 14.5 | 19.2 | 3.0 | 0.9 |
| F | 16.0 | 0.0 | 14.5 | 0.0 | — | 3.0 | 0.0 |

Example 7

Preparation of $Ce_2O_3/MgO/\alpha/\theta$-$Al_2O_3$ Catalyst Support Samples G-K These supports were prepared as in Example 6 with the exception that $\delta/\theta$-$Al_2O_3$ 4×4 mm tablet form was used instead of $\delta$-$Al_2O_3$. The surface area of the $\delta/\theta$-$Al_2O_3$ was 20 $m^2$/g. The catalyst supports were calcined, in air as shown below:

| Temperature | Time |
|---|---|
| 120° C. | 16 hr |
| 240° C. | 2 hr |
| 550° C. | 6 hr |

The compositions of the catalyst supports are shown in Table VI.

TABLE VI

| Sample # | $Mg(NO_3)_2 \cdot 6H_2O$ (grams) | $Ce(NO_3)_3 \cdot 6H_2O$ (grams) | Citric Acid $H_2O$ (grams) | Mg: Ce (molar) | Mg (wt %) | Ce (wt %) |
|---|---|---|---|---|---|---|
| G | 16.0 | 2.70 | 14.5 | 10.0 | 3.0 | 1.7 |
| H | 8.0 | 1.37 | 7.3 | 9.9 | 1.5 | 0.9 |
| I | 16.0 | 5.55 | 14.5 | 4.9 | 3.0 | 3.6 |
| J | 16.0 | 1.37 | 14.5 | 19.8 | 3.0 | 0.9 |
| K | 16.0 | 0.00 | 0.00 | — | 3.0 | 0.0 |

Example 8

Preparation of Catalyst L by Addition of Pd to Catalyst Support H 24 g of sample H were added to a 250 ml beaker. 1.43 g. Pd solution (0.5 wt % Pd) was added to a separate beaker. 6.5 g. distilled water was also added to the beaker. The Pd/$H_2O$ solution was added dropwise to catalyst support Sample H, with constant stirring. The Pd/Sample H material was then dried at 130° C. for 2 hours followed by calcination in air under the conditions shown below to produce Sample L.

| Temperature | Time |
|---|---|
| 120° C. | 16 hr. |
| 225° C. | 1 hr. |
| 352° C. | 4 hr. |

Example 9

Performance of Sample L 20 cc of catalyst Sample L were loaded into a stainless steel reactor. Catalyst Sample L was reduced under hydrogen at 409° F. for 3 hours and was then allowed to cool. The reactor temperature was then raised to 98° F. and $H_2$ (200 cc/min) hydrocarbon (700 cc/min) feeds were begun. The pressure was maintained at 200 psig. The reactor temperature increased very rapidly above 120° C.

TABLE VII

Performance of Catalyst L: 0.3% Pd on Ce: Mg/α-Al$_2$O$_3$

| | First Feed Analysis | Reactor Temperature 120° F. | 115° F. |
|---|---|---|---|
| | | FID (wt %) | |
| $C_6^+$ | 0.0 | 0.1 | 0.2 |
| $C_1$ | 20.2 | 20.1 | 20.2 |
| $C_2 + C_2^=$ | 55.4 | 55.9 | 56.0 |
| $C_3^+$ Acetylene | 0.4 | 1.2 | 0.1 |
| $C_3^=$ | 23.2 | 23.5 | 23.3 |
| Propadiene (PD) | 0.4 | 0.1 | 0.1 |
| Methyl acetylene (MA) | 0.4 | 0.0 | 0.0 |
| $C_4$s | 0.0 | 0.0 | 0.0 |
| PD + MA | 0.8 | 0.1 | 0.1 |
| | | TCD (wt %) | |
| $C_2^=$ | 69.8 | 68.7 | 69.4 |
| $C_2$ | 0.0 | 1.9 | 1.2 |
| Acetylene | 0.6 | 0.0 | 0.0 |
| $C_1$ | 29.6 | 29.4 | 29.4 |
| | | Conversion and Selectivity | |
| % PD conversion | — | 79.6 | 70.8 |
| % MA conversion | — | 94.9 | 93.7 |
| % MAPD conversion | — | 87.5 | 82.6 |
| % $C_2^=$ selectivity | — | −844.6 | −67.9 |
| $C_2^=$ | 55.4 | 54.4 | 55.0 |
| $C_2$ make | — | 1.5 | 0.9 |

The data in Table VII illustrates that Catalyst L converted about 71 percent propadiene to methyl acetylene at 115° F. However, the catalyst accomplished this with a small net loss in ethylene.

Example 10

Addition of Ag to Sample L

After being screened for ARU activity as described in Example 9, the catalyst was removed from the reactor and calcined, in air, according to the schedule below:

| Temperature | Time |
|---|---|
| 130° C. | 2 hr. |
| 240° C. | 2 hr. |
| 360° C. | 4 hr. |

The catalyst was allowed to cool for about 10 hours. The catalyst, which weighed 20.4 g, was then poured into a 100 cc beaker. A solution of 97 mg. of $AgNO_3$ in 10.8 g of distilled water was added to a 25 cc beaker. The $AgNO_3$ solution was then added to the catalyst. The mixture was allowed to sit for 30 minutes and was then filtered. The catalyst was placed in a drying oven at 120° C. for 90 min. and was then loaded into a quartz calcining tube and calcined, in air, as shown below:

| Temperature | Time |
|---|---|
| 120° C. | 1.5 hr. |
| 180° C. | 0.5 hr. |
| 410° C. | 3.0 hr. |

The resulting catalyst, referred to as Sample M, was transferred directly to a reactor upon cooling.

Example 11

Performance of Sample M 20 cc of Sample M was loaded into a stainless steel reactor. Sample M was reduced at 400° F. for three hours immediately before screening. The reactor was heated under reaction conditions of 200 cc/min. $H_2$, 700 cc/min and pressure of 200 psig in the presence of a first hydrocarbon feed. After reaching a temperature of about 178° F., the reactor was allowed to cool to room temperature and maintained under 50 cc/min. $H_2$ for at least 48 hours. Thereafter, the reactor was again heated under reaction conditions of 200 cc/min. $H_2$, 700 cc/min, and 200 psig in the presence of a second hydrocarbon feed. The feed compositions and the product compositions at different reaction temperatures are shown in Table VIII. FIG. 1 shows a graph of ethylene production as a function of reaction temperature for the first and second feed. As seen in FIG. 1, $T_2$ is 188° F.

TABLE VIII

Performance of Catalyst M: 0.3% Pd/0.15% Ag on Ce: Mg/α-Al$_2$O$_3$

| | First Feed Analysis | Run #1 | Run #2 | Run #3 | Run #4 | Second Feed Analysis | Run #5 | Run #6 | Run #7 | Run #8 | Run #9 | Run #10 |
|---|---|---|---|---|---|---|---|---|---|---|---|---|
| | | Temperature (° F.) | | | | | Temperature (° F.) | | | | | |
| | | 138 | 144 | 153 | 178 | | 140 | 146 | 182 | 196 | 155 | 165 |
| | | FID (wt %) | | | | | | | | | | |
| $C_6^+$ | 0.0 | 0.1 | 0.1 | 0.1 | 0.1 | 0.0 | 0.1 | 0.1 | 0.0 | 0.0 | 0.0 | 0.0 |
| $C_1$ | 20.2 | 20.1 | 20.2 | 20.2 | 20.1 | 15.6 | 15.4 | 15.4 | 15.4 | 15.4 | 15.4 | 15.4 |
| $C_2 + C_2^=$ | 55.4 | 56.2 | 56.0 | 56.0 | 56.0 | 52.1 | 52.1 | 52.9 | 52.7 | 52.7 | 52.7 | 52.7 |
| $C_3^+$ Acetylene | 0.4 | 0.1 | 0.1 | 0.1 | 0.2 | 0.4 | 0.1 | 0.1 | 0.3 | 0.5 | 0.2 | 0.2 |

TABLE VIII-continued

Performance of Catalyst M: 0.3% Pd/0.15% Ag on Ce: Mg/α-Al$_2$O$_3$

| | First Feed Analysis | Run #1 | Run #2 | Run #3 | Run #4 | Second Feed Analysis | Run #5 | Run #6 | Run #7 | Run #8 | Run #9 | Run #10 |
|---|---|---|---|---|---|---|---|---|---|---|---|---|
| | | Temperature (° F.) | | | | | Temperature (° F.) | | | | | |
| | | 138 | 144 | 153 | 178 | | 140 | 146 | 182 | 196 | 155 | 165 |
| C$_3^=$ | 23.1 | 23.3 | 23.5 | 23.6 | 23.6 | 31.1 | 31.4 | 31.5 | 31.6 | 31.3 | 31.5 | 31.7 |
| Propadiene (PD) | 0.4 | 0.0 | 0.0 | 0.1 | 0.0 | 0.4 | 0.0 | 0.0 | 0.0 | 0.0 | 0.0 | 0.0 |
| Methyl acetylene (MA) | 0.4 | 0.2 | 0.1 | 0.0 | 0.0 | 0.4 | 0.1 | 0.0 | 0.0 | 0.0 | 0.0 | 0.0 |
| C$_4$s | 0.0 | 0.0 | 0.0 | 0.0 | 0.0 | 0.0 | 0.0 | 0.0 | 0.0 | 0.0 | 0.0 | 0.0 |
| PD + MA | 0.9 | 0.2 | 0.1 | 0.0 | 0.0 | 0.8 | 0.1 | 0.1 | 0.0 | 0.0 | 0.0 | 0.0 |
| | | | | | | TCD (wt %) | | | | | | |
| C$_2^=$ | 70.3 | 70.6 | 70.4 | 70.2 | 68.2 | 74.2 | 74.5 | 74.4 | 71.8 | 69.2 | 74.0 | 73.5 |
| C$_2$ | 0.0 | 0.2 | 0.3 | 0.6 | 2.7 | 0.0 | 0.3 | 0.5 | 3.1 | 5.7 | 0.8 | 1.3 |
| Acetylene | 0.6 | 0.0 | 0.0 | 0.0 | 0.0 | 0.6 | 0.0 | 0.0 | 0.0 | 0.0 | 0.0 | 0.0 |
| C$_1$ | 29.2 | 29.2 | 29.2 | 29.2 | 29.2 | 25.2 | 25.2 | 25.2 | 25.1 | 25.1 | 25.2 | 25.2 |
| | | | | | | Conversion and Selectivity | | | | | | |
| % PD conversion | — | 91.8 | 95.0 | 97.0 | 100.0 | — | 90.5 | 92.3 | 100 | 100 | 93.8 | 96.4 |
| % MA conversion | — | 55.9 | 81.2 | 93.1 | 98.6 | — | 83.2 | 90.1 | 98.1 | 98.9 | 96.0 | 97.9 |
| % MAPD conversion | — | 74.1 | 88.3 | 95.1 | 99.3 | — | 86.7 | 91.1 | 99.0 | 99.3 | 95.0 | 97.2 |
| % C$_2^=$ selectivity | — | 64.1 | 32.1 | −11.8 | −365.2 | — | 42.3 | 24.0 | −389.6 | −806.2 | −34.5 | −118.7 |
| C$_2^=$ | 55.4 | 56.0 | 55.8 | 55.6 | 53.9 | 52.0 | 52.7 | 52.6 | 50.5 | 48.7 | 52.2 | 51.8 |
| C$_2$ make | — | 0.2 | 0.3 | 0.5 | 2.1 | — | 0.2 | 0.3 | 2.2 | 4.0 | 0.6 | 0.9 |

Feed flow rate is 700 cc/min; H$_2$ flow rate is 200 cc/min. The carbon monoxide content in the hydrocarbon feed was 385 ppm (300 ppm in the reactor).

The data in Table II combined with FIG. 1 indicate that Catalyst M has a T$_1$ of about 140° F.; a T$_2$ of about 188° F.; and thus a ΔT of about 48° F.

Comparative Example 12

Preparation of Comparative Sample N 1.8 grams of a 0.5 wt % Pd solution were added dropwise to 30 grams of α-Al$_2$O$_3$ pellets having a surface area of 20 m$^2$/g. The Pd/Al$_2$O$_3$ composition was then dried in a drying oven at 130° C. for 2 hours. The Pd/Al$_2$O$_3$ composition was then calcined in air in a quartz calcining tube according to the following schedule: 16 hours at 120° C., 2 hours at 240° C., and 6 hours at 360° C. The Pd/Al$_2$O$_3$ composition was then allowed to cool. 140 grams of AgNO$_3$ were dissolved in 15.9 grams of distilled water. The AgNO$_3$ solution was poured into a beaker containing the Pd/Al$_2$O$_3$ composition and the beaker was allowed to stand for 30 minutes. The solution was then filtered and the remaining solid Pd/Ag/Al$_2$O$_3$ catalyst was again calcined. The second calcination occurred in air and proceeded as follows: 2 hours at 120° C., 2 hours at 240° C., 1 hour at 350° C., and 4 hours at 400° C. The resulting Pd/Ag/Al$_2$O$_3$ catalyst is called Comparative Sample N.

TABLE IX

Performance of Catalyst N: 0.3% Pd/0.15% Ag Pd/Ag on α-Al$_2$O$_3$

| | Feed Analysis | Temperature (° F.) | | | | | | | |
|---|---|---|---|---|---|---|---|---|---|
| | | 85 | 114 | 94 | 106 | 110 | 113 | 147 | 165 |
| | | FID (wt %) | | | | | | | |
| C$_6^+$ | 0.01 | 0.0 | 0.0 | 0.0 | 0.0 | 0.0 | 0.1 | 0.1 | 0.1 |
| C$_1$ | 15.6 | 15.4 | 15.4 | 15.4 | 15.4 | 15.4 | 15.4 | 15.5 | 15.5 |
| C$_2$ + C$_2^=$ | 51.9 | 52.8 | 52.9 | 52.9 | 52.9 | 53.0 | 52.9 | 52.7 | 52.6 |
| C$_3^+$ Acetylene | 0.4 | 0.2 | 0.1 | 0.1 | 0.1 | 0.1 | 0.1 | 0.2 | 0.4 |
| C$_3^=$ | 31.2 | 30.8 | 31.4 | 30.9 | 31.1 | 31.2 | 31.3 | 31.6 | 31.6 |
| Propadiene (PD) | 0.4 | 0.0 | 0.2 | 0.4 | 0.3 | 0.3 | 0.2 | 0.0 | 0 |
| Methyl acetylene (MA) | 0.4 | 0.4 | 0.0 | 0.3 | 0.1 | 0.1 | 0.0 | 0.0 | 0.0 |
| C$_4$s | 0.0 | 0.0 | 0.0 | 0.0 | 0.0 | 0.0 | 0.0 | 0.0 | 0.0 |
| PD + MA | 0.8 | 0.7 | 0.2 | 0.7 | 0.5 | 0.3 | 0.3 | 0.0 | 0.0 |
| | | TCD (wt %) | | | | | | | |
| C$_2^=$ | 74.1 | 74.4 | 74.2 | 74.6 | 74.6 | 74.6 | 74.4 | 71.7 | 68.8 |
| C$_2$ | 0.0 | 0.0 | 0.5 | 0.0 | 0.0 | 0.2 | 0.3 | 3.1 | 6.0 |
| Acetylene | 0.7 | 0.3 | 0.0 | 0.1 | 0.0 | 0.0 | 0.0 | 0.0 | 0.0 |
| C$_1$ | 25.3 | 25.3 | 25.3 | 25.3 | 25.3 | 25.2 | 25.6 | 25.3 | 25.2 |
| | | Conversion and Selectivity | | | | | | | |
| % PD conversion | — | 8.4 | 52.2 | 11.5 | 21.4 | 34.6 | 38.4 | 97.0 | 100.0 |
| % MA conversion | — | 14.9 | 94.8 | 30.0 | 67.9 | 88.4 | 91.5 | 100.0 | 98.4 |
| % MAPD conversion | — | 11.8 | 74.3 | 21.1 | 45.5 | 62.6 | 66.0 | 98.5 | 99.1 |

TABLE IX-continued

Performance of Catalyst N: 0.3% Pd/0.15% Ag Pd/Ag on α-Al$_2$O$_3$

| | Feed Analysis | Temperature (° F.) | | | | | | | |
|---|---|---|---|---|---|---|---|---|---|
| | | 85 | 114 | 94 | 106 | 110 | 113 | 147 | 165 |
| % C$_2$⁻ selectivity | — | 88.6 | 18.9 | 103.7 | 77.1 | 73.4 | 50.7 | −357.7 | −781.1 |
| C$_2$⁻ | 51.9 | 52.8 | 52.5 | 52.9 | 52.8 | 52.8 | 52.7 | 50.5 | 48.4 |
| C$_2$ make | — | 0.0 | 0.4 | 0.0 | 0.1 | 0.2 | 0.2 | 2.2 | 4.2 |

Feed flow rate is 700 cc/min; H$_2$ flow rate is 200 cc/min

Comparative Example 13

Figure 2:
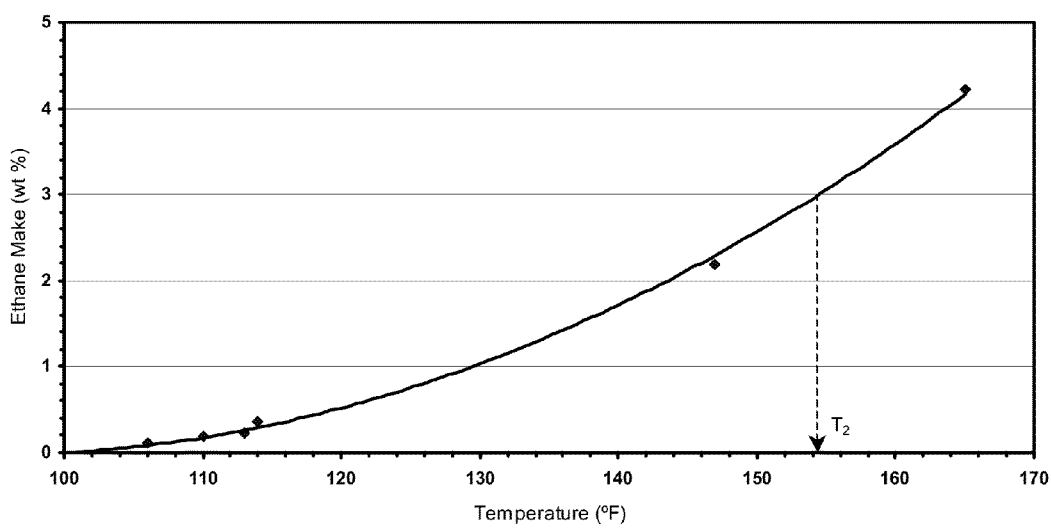
FIG. 2 is a graph of ethane production as a function of temperature for Comparative Sample N discussed in Example 13.

Screening of Comparative Sample N 20 cc Comparative Sample N was loaded into a stainless steel reactor. Comparative Sample N was reduced at 409° F. for three hours under H$_2$ flow of 100 cc/min. The reactor was then allowed to cool and the product compositions at 85° F. and 114° F. were recorded. The reactor was maintained under H$_2$ at 50 cc/min. for at least 8 hours. The reactor was then heated again. The reactor conditions were hydrocarbon feed of 700 cc/min., H$_2$ feed of 200 cc/min. and a pressure of 200 psig. The feed composition and the product compositions as a function of temperature are shown in Table IX. FIG. 2 shows a graph of ethylene production as a function of reaction temperature. As seen in FIG. 2, T$_2$ is 154° F.

Table X below illustrates the dehydrogenation activity of Sample M and Comparative Sample N.

TABLE X

| Catalyst | 0.3% Pd/0.15% Ag | 0.3% Pd/0.15% Ag |
|---|---|---|
| Support | α-Al$_2$O$_3$ | 2.5% Ce + Mg on |
| Sample | Comp. Sample N | α-Al$_2$O$_3$ Sample M |
| T$_1$ | 110° F. | 140° F. |
| T$_2$ | 154° F. | 188° F. |
| Δ T | 44° F. | 48° F. |
| % Propadiene conversion | 34.6 | 90.5 |
| % Methylacetylene conversion | 88.4 | 83.2 |
| % MAPD conversion | 62.5 | 86.7 |
| % C$_2$⁻ selectivity | 73.4 | 42.3 |

While the invention has been described with respect to a limited number of embodiments, the specific features of one embodiment should not be attributed to other embodiments of the invention. No single embodiment is representative of all aspects of the inventions. In some embodiments, the compositions may include numerous compounds not mentioned herein. In other embodiments, the compositions do not include, or are substantially free of, any compounds not enumerated herein. Variations and modifications from the described embodiments exist. The method of making the catalysts is described as comprising a number of acts or steps. These steps or acts may be practiced in any sequence or order unless otherwise indicated. Finally, any number disclosed herein should be construed to mean approximate, regardless of whether the word "about" or "approximately" is used in describing the number. The appended claims intend to cover all those modifications and variations as falling 7 within the scope of the invention.

What is claimed is:

1. A process for the selective hydrogenation of highly unsaturated hydrocarbons to less unsaturated hydrocarbons which comprises the step of:
    contacting in the presence of hydrogen a hydrocarbon-containing fluid comprising one or more highly unsaturated hydrocarbons with a catalyst composition comprising cerium and magnesium, a Mg:Ce molar ratio of between about 0.01:1 to about 20:1, an inorganic support having a surface area greater than 10 m$^2$/g and less than or equal to about 400 m$^2$/g and a particle size of between about 0.5 mm and about 10 mm.

2. The process of claim 1 wherein the highly unsaturated hydrocarbon is selected from the group consisting of alkynes, dienes, and mixtures thereof.

3. The process of claim 1 wherein the hydrocarbon-containing fluid further comprises one or more impurities selected from the group consisting of carbon monoxide, hydrogen sulfide, carbonyl sulfide, carbon disulfide, mercaptans, organic sulfides, organic disulfides, organic polysulfides, thiophene, organic trisulfides, and organic tetrasulfides.

4. The process of claim 1 wherein the hydrocarbon-containing fluid further comprises at least about 50 wt % ethylene.

5. The process of claim 1 wherein the hydrocarbon-containing fluid further comprises at least about 85 wt % propylene.

6. The process of claim 1 wherein the hydrocarbon-containing fluid comprises between about 0.1 and about 15 wt % methylacetylene; and wherein at least about 50 wt % of the methyl acetylene is hydrogenated; and wherein at least about 45 wt % of the hydrogenated methyl acetylene is converted into propylene.

7. The process of claim 1 wherein the hydrocarbon-containing fluid comprises between about 0.1 and about 2 wt % propadiene.

8. The process of claim 1 wherein step (1) occurs under conditions of a pressure from about 15 psig to about 2,000 psig; a temperature of from about 10° C. to about 300° C.; and wherein the gas hourly space velocity of the hydrocarbon-containing fluid is at least about 1 liter of hydrocarbon-containing fluid per liter of catalyst per hour.

9. The process of claim 1 wherein the catalyst composition further comprises silver.

10. The process of claim 1 wherein the catalyst composition further comprises an alkali metal.

11. A process for the isomerization of highly unsaturated hydrocarbons to other highly unsaturated hydrocarbons which comprises the step of:
    contacting in the presence of hydrogen a hydrocarbon-containing fluid comprising one or more highly unsaturated hydrocarbons with a catalyst composition comprising cerium and magnesium, a Mg:Ce molar ratio of between about 0.01:1 to about 20:1, an inorganic support having a surface area greater than 10 m²/g and less than or equal to about 400 m²/g and a particle size of between about 0.5 mm and about 10 mm.

12. The process of claim 11 wherein the highly unsaturated hydrocarbon is selected from the group consisting of alkynes, diolefins, and mixtures thereof.

13. The process of claim 11 wherein the hydrocarbon-containing fluid comprises acetylene and methylacetylene.

14. The process of claim 11 wherein the highly unsaturated hydrocarbon comprises between about 10 ppb (by weight) and about 5 wt % of the hydrocarbon-containing fluid.

15. The process of claim 11 wherein the hydrocarbon-containing fluid comprises at least about 85 wt % propylene; and wherein at least about 50 wt % of the total highly unsaturated hydrocarbon is isomerized.

16. The process of claim 11 wherein the hydrocarbon-containing fluid comprises at least about 50 wt % ethylene; and wherein at least about 50 wt % of the total highly unsaturated hydrocarbon is isomerized.

17. The process of claim 11 wherein the hydrocarbon-containing fluid comprises propadiene; wherein at least about 50 wt % of the propadiene is isomerized; and wherein at least about 20 wt % of the isomerized propadiene is converted to methylacetylene.

18. The process of claim 11 wherein contacting step (1) occurs under conditions of a pressure from about 15 psig to about 2,000 psig; a temperature of from about 10° C. to about 300° C.; wherein the hydrogen gas is present in an amount between about 0.1 to about 1,000 moles hydrogen per mole of highly unsaturated hydrocarbon; and wherein the gas hourly space velocity of the hydrocarbon-containing fluid is at least about 1 liter of hydrocarbon-containing fluid per liter of catalyst per hour.

19. The process of claim 11 wherein the catalyst composition further comprises silver, an alkali metal, or a combination thereof.

20. A hydrogenation catalyst comprising cerium and magnesium, a Mg:Ce molar ratio of between about 0.01:1 to about 20:1, an inorganic support having a surface area greater than 10 m²/g and less than or equal to about 400 ml/g and a particle size of between about 0.5 mm and about 10 mm.

21. The hydrogenation catalyst of claim 20, wherein the cerium and magnesium are incorporated into, onto or with the inorganic support.

22. The hydrogenation catalyst of claim 21 wherein the inorganic support has a pore volume of between about 0.05 mL/gm and about 2 mL/gm and a pore diameter of between about 5 angstroms and about 600 angstroms.

23. The hydrogenation catalyst of claim 20 further comprising palladium present in an amount between about 0.0001 to about 3 wt % of the total catalyst composition.

24. The hydrogenation catalyst of claim 23 further comprising silver present in an amount between about 0.0001 to about 20 wt % of the total catalyst composition; wherein the silver:palladium weight ratio is between about 0.1:1 and about 20:1.

25. The hydrogenation catalyst of claim 24 further comprising an alkali metal compound present in an amount between about 0.001 and about 10 wt % of the total catalyst composition; wherein the alkali metal:palladium weight ratio is between about 0.5:1 and about 500:1.

26. The hydrogenation catalyst of claim 23 further comprising an alkali metal compound present in an amount between about 0.001 and about 10 wt % of the total catalyst composition; wherein the alkali metal:palladium weight ratio is between about 0.5:1 and about 500:1.

27. The hydrogenation catalyst of claim 20, wherein the hydrogenation catalyst is catalytically effective to selectively hydrogenate methyl acetylene to propylene, acetylene to ethylene, or a combination thereof.

28. An isomerization catalyst comprising cerium and magnesium, a Mg:Ce molar ratio of between about 0.01:1 to about 20:1, an inorganic support having a surface area greater than 10 m²/g and less than or equal to about 400 m²/g and a particle size of between about 0.5 mm and about 10 mm.

29. The isomerization catalyst of claim 28, wherein the inorganic support has a pore volume of between about 0.05 mL/gm and about 1 mL/gm and a pore diameter of between about 5 angstroms and about 600 angstroms.

30. The isomerization catalyst of claim 28 further comprising palladium present in an amount between about 0.0001 to about 3 wt % of the total catalyst composition.

31. The isomerization catalyst of claim 30 further comprising silver present in an amount between about 0.0001 to about 20 wt % of the total catalyst composition; wherein the silver:palladium weight ratio is between about 0.1:1 and about 20:1.

32. The isomerization catalyst of claim 31 further comprising an alkali metal compound, wherein the alkali metal compound is present in an amount between about 0.001 and about 10 wt % of the total catalyst composition; and wherein the alkali metal:palladium weight ratio is between about 0.5:1 and about 500:1.

33. The isomerization catalyst of claim 30 further comprising an alkali metal compound, wherein the alkali metal compound is present in an amount between about 0.001 and about 10 wt % of the total catalyst composition; and wherein the alkali metal:palladium weight ratio is between about 0.5:1 and about 500:1.

34. A process of producing a catalyst comprising cerium and magnesium, a Mg:Ce molar ratio of between about 0.01:1 to about 20:1, an inorganic support having a surface area greater than 10 m²/g and less than or equal to about 400 m²/g and a particle size of between about 0.5 mm and about 10 mm, said process comprising the steps of:
  (1) mixing a cerium-containing compound, a magnesium-containing compound, citric acid component and water; wherein the Mg:Ce molar ratio is between about 0.01:1 to about 20:1;
  (2) subjecting the mixture from step (1) to melting conditions to obtain a molten mixture;
  (3) subjecting the molten mixture to evaporating conditions;
  (4) subjecting the mixture obtained in step (3) to drying conditions to obtain a dried catalyst; and
  (5) subjecting the dried catalyst to calcining conditions to produce a calcined catalyst;
  (6) preparing an aqueous solution containing palladium;
  (7) adding the aqueous solution to the calcined catalyst; and
  (8) drying the product of step (7).

35. The process of claim 34 further comprising the steps of:
  (9) preparing an aqueous solution containing silver;
  (10) adding the aqueous solution containing silver to the product of step (8);
  (11) drying the product of step (10); and
  (12) calcining the product of step (11).

36. A process of producing a catalyst comprising cerium and magnesium, a Mg:Ce molar ratio of between about 0.01:1 to about 20:1, an inorganic support having a surface area greater than 10 m²/g and less than or equal to about 400 m²/g and a particle size of between about 0.5 mm and about 10 mm, said process comprising the steps of:

(1) mixing a cerium-containing compound, a magnesium-containing compound, citric acid component and water; wherein the Mg:Ce molar ratio is between about 0.01:1 to about 20:1;
(2) subjecting the mixture from step (1) to melting conditions to obtain a molten mixture;
(3) contacting an inorganic support with the molten mixture;
(4) subjecting the inorganic support and molten mixture obtained in step (3) to drying conditions to obtain a dried catalyst; and
(5) subjecting the dried catalyst to calcining conditions to produce a calcined catalyst.

37. The process of claim 36 further comprising the steps of:
(6) preparing an aqueous solution containing palladium;
(7) adding the aqueous solution to the calcined catalyst; and
(8) drying the product of step (7).

38. The process of claim 37 further comprising the steps of:
(9) preparing an aqueous solution containing silver;
(10) adding the aqueous solution containing silver to the product of step (8);
(11) drying the product of step (10); and
(12) calcining the product of step (11).

* * * * *